US011149090B2

(12) United States Patent
Ellmark et al.

(10) Patent No.: US 11,149,090 B2
(45) Date of Patent: Oct. 19, 2021

(54) COMBINATION THERAPIES WITH ANTI CD40 ANTIBODIES

(71) Applicant: ALLIGATOR BIOSCIENCE AB, Lund (SE)

(72) Inventors: Peter Ellmark, Lund (SE); Per Norlen, Lund (SE); Niina Veitonmaki, Lund (SE)

(73) Assignee: ALLIGATOR BIOSCIENCE AB, Lund (SE)

( * ) Notice: Subject to any disclaimer, the term of this patent is extended or adjusted under 35 U.S.C. 154(b) by 47 days.

(21) Appl. No.: 15/329,402

(22) PCT Filed: Aug. 12, 2015

(86) PCT No.: PCT/EP2015/068598
§ 371 (c)(1),
(2) Date: Jan. 26, 2017

(87) PCT Pub. No.: WO2016/023960
PCT Pub. Date: Feb. 18, 2016

(65) Prior Publication Data
US 2017/0226217 A1    Aug. 10, 2017

(30) Foreign Application Priority Data

Aug. 12, 2014  (GB) ..................................... 1414270
Dec. 18, 2014  (GB) ..................................... 1422614
May 1, 2015    (GB) ..................................... 1507541

(51) Int. Cl.
C07K 16/28     (2006.01)
A61K 39/395    (2006.01)
A61K 45/06     (2006.01)
A61K 39/00     (2006.01)

(52) U.S. Cl.
CPC ...... *C07K 16/2878* (2013.01); *A61K 39/3955* (2013.01); *A61K 45/06* (2013.01); *C07K 16/2818* (2013.01); *A61K 2039/505* (2013.01); *A61K 2039/507* (2013.01); *C07K 2317/56* (2013.01); *C07K 2317/565* (2013.01); *C07K 2317/73* (2013.01); *C07K 2317/732* (2013.01); *C07K 2317/75* (2013.01); *C07K 2317/76* (2013.01); *C07K 2317/90* (2013.01)

(58) Field of Classification Search
None
See application file for complete search history.

(56) References Cited

U.S. PATENT DOCUMENTS

| 6,312,693 | B1 | 11/2001 | Aruffo et al. |
| 9,676,862 | B2 | 6/2017 | Ellmark et al. |
| 2004/0110226 | A1 | 6/2004 | Lazar et al. |
| 2004/0132066 | A1 | 7/2004 | Balint et al. |
| 2006/0166198 | A1 | 7/2006 | Furebring et al. |
| 2011/0027276 | A1 | 2/2011 | Bernett et al. |
| 2012/0225014 | A1 | 9/2012 | Bedian et al. |

FOREIGN PATENT DOCUMENTS

| EP | 1885399 | 2/2008 |
| EP | 2011802 | 4/2009 |
| WO | 2001083755 | 11/2001 |
| WO | 2002048351 | 6/2002 |
| WO | 2003097834 | 11/2003 |
| WO | 2006073443 | 7/2006 |
| WO | 2006/121168 A1 | 11/2006 |
| WO | 2006128103 | 11/2006 |
| WO | 2008051424 | 5/2008 |
| WO | 2009094391 | 7/2009 |
| WO | 2010024676 | 3/2010 |
| WO | 2013/019906 A9 | 2/2013 |
| WO | 2013034904 | 3/2013 |
| WO | 2013/132044 A1 | 9/2013 |
| WO | 2014121099 | 8/2014 |
| WO | 2015/091655 A1 | 6/2015 |
| WO | 2015/200119 A1 | 12/2015 |
| WO | 2016/161239 A1 | 10/2016 |
| WO | 2016/168716 A1 | 10/2016 |
| WO | 2016/196314 A1 | 12/2016 |
| WO | 2017/004006 A1 | 1/2017 |
| WO | 2017/004016 A1 | 1/2017 |

OTHER PUBLICATIONS

McDermott et al (Cancer Med., 2:662-673, 2013).*
Neron et al., Tuning of CD40-CD154 Interactions in Human B-Lymphocyte Activation: A Broad Array of In Vitro Models for a Complex In Vivo Situation, Archivum Immunologiae et Therapiae Experimentalis, 2011, 25-40, 59.
Huang et al., Sensitization of SiHa cell to gemcitabine by CD40 activation and its overexpression in cervical carcinoma. Medical Oncology, 2010, 781-788, 28.
Huout et al., Immunomodulating antibodies and drugs for the treatment of hematological malignancies, Cancer Metastasis Rev. 2011, 97-109, 30.
Rudikoff et al., "Single amino acid substitution altering antigen-binding specificity" Proc. Natl. Acad. Sci., 1982, 1979-1983, 79.
Kussie, et al., "A Single Engineered Amino Acid Substitution Changes Antibody Fine Specificity" J. Immunol., 1994, 146-152, 152.
Chen et al., "Enhancement and destruction of antibody function by somatic mutation: unequal occurrence is controlled by V gene combinatorial associations" EMBO J., 1995, 2784-2794, 14.

(Continued)

*Primary Examiner* — Brian Gangle
(74) *Attorney, Agent, or Firm* — Robert C. Netter, Jr.; Dann, Dorfman, Herrell & Skillman

(57) ABSTRACT

The present invention relates to combination therapies for treating a solid tumour in a subject. The combination therapies comprise (a) an antibody, or antigen-binding portion thereof, that specifically binds to CD40, and (b) a further immunotherapeutic agent with efficacy in the treatment of cancer, which agent is not an anti-CD40 antibody or antigen-binding fragment thereof. The invention also relates to a kits and methods of using such therapies.

16 Claims, 13 Drawing Sheets

Specification includes a Sequence Listing.

(56) References Cited

OTHER PUBLICATIONS

Colman, "Effects of Amino Acid Changes on Antibody-Antigen Interactions" res. Immunol., 1994, 33-36, 145.
VonderHeide et al., "Agonistic CD40 Antibodies and Cancer Therapy" Clin. Cancer Res., 2013, 1035-1043, 19.
Sandin et al., "Locally Delivered CD40 Agonist Antibody Accumulates in Secondary Lymphoid Organs and Eradicates Experimental Disseminated Bladder Cancer" Cancer Immunol, Res., 2014, 80-90, 2.
Moran et al., "The TNFRs OX40, 4-1BB, and CD40 as targets for cancer immunotherapy" Curr. Opin. Immunol., 2013, 230-237, 25.
Gerloni et al., "Functional cooperation between T helper cell determinants" Proc. Natl. Acad. Sci., 2000, 13269-13274, 97.
Mangsbo, et al., "ADC-1013, an agonistic CD40 antibody optimized for local immunothrerapy of cancer," J. Immunotherapy Cancer, 2013, p. 42, 1.
Uno et al., "Eradication of established tumors in mice by a combination antibody-based therapy" Nat. Med., 2006, 693-698, 12.
Bajor et al., "Abstract CT137: Combination of agonistic CD40 monoclonal antibody CP-870,893 and anti-CTLA-4 antibody tremelimumab in patients with metastatic melanoma," Cancer Res., 2015, Abstract CT137, 75.
Chonan et al., "CD40/CD40L expression correlates with the survival of patients with glioblastomas and an augmentation in CD40 signaling enhances the efficacy of vaccinations against glioma models" Neuro-Oncology, 2015, 1453-1462, 17.
Sorensen et al., "Adenoviral vaccination combined with CD40 stimulation and CTLA-4 blockage can lead to complete tumor regression in a murine melanoma model," Vaccine, 2010, 6757-6764, 28.
Burrocchi et al., "Intratumor OX40 stimulation inhibits IRF1 expression and IL-10 production by Treg cells while enhancing CD40L expression by effector memory T cells," Eur. J. Immunology, 2011, 3615-3626, 41.
Advani et al., Phase I Study of the humanized anti-CD40 monoclonal antibody Dacetuzumab in refractory of recurrent non-hodgkin's lymphoma, J Clinical Oncology, 2009, 4371-4377, 27.
Armitage et al., Molecular and biological characterization of a murine ligand for CD40, Nature, 1992, 80-82, 357.
Bajorath et al., Detailed comparison of two molecular models of the human CD40 ligand with an x-ray structure and critical assessment of model-based mutagenesis and residue mapping studies, J Biol Chem , 1998, 24603-9, 273.
Bajorath et al., Identification of residues on CD40 and its ligand which are critical for the receptor-ligand interaction, Biochemistry, 1995, 1833-44, 34.
Diehl et al., CD40 activation in vivo overcomes peptide-induced peripheral cytotoxic T-lymphocyte tolerance and augments anti-tumor vaccine efficacy, Nat. Med., 1999, 774-779, 5.
Ellmark et al., Identification of a Strongly Activating Human Anti-Cd40 Antibody that Suppresses HIV Type 1 Infection, AIDS Research and Human Rettroviruses, 2008, 367-373, 24(3).
Ellmark et al., Modulation of the CD40-CD40L ligand interaction using human anti-CD40 single-chain antibody fragments obtained from the n-CoDeR® phage display library, Immunology, 2002, 456-463, 106.
Fellouse et al., High-throughput generation of synthetic antibodies from highly functional minimalist phage-displayed libraries, J Mo/ Biol, 2007, 924-940, 373.
Francisco et al., Agonistic properties and in vivo antitumor activity of the anti-CD40 antibody SGN-14, Cancer Research, 2000, 3225-3231, 60.
French et al., CD40 antibody evokes a cytotoxic T-cell response that eradicates lymphoma and bypasses T-cell help, Nat Med, 1999, 548-53, 5.
Quezada et al., CD40/CD154 interactions at the interface of tolerance and immunity, Annu. Rev. Immunol., 2004, 307-328, 22.
Siepmann et al., Rewiring CD40 is necessary for delivery of rescue signals to B cells in germinal centres and subsequent entry into the memory pool, Immunology, 2001, 263-72, 102(3).
Tong et al., Prospects for CD40-derived experimental therapy of human cancer, Cancer Gene Therapy, 2003, 1-13, 10(1).
Van Mierlo et al., CD40 stimulation leads to effective therapy of CD40(-) tumors through induction of strong systemic cytotoxic T lymphocyte immunity, Proc. Natl. Acad. Sci. U. S. A., 2002, 5561-5566, 99.
White et al., Interaction with FcCRIIB is critical for the agonistic activity of anti-CD40 monoclonal antibody, Journal of Immunology, 2011, 1754-1763, 187.
Allen et al., CD40 ligand gene defects responsible for X-linked hyper-IgM syndrome, Science, 1993, 990-993, 259.
Bajorath et al., Analysis of gp39/CD40 interactions using molecular models and site-directed mutagenesis, Biochemistry, 1995, 9884-92, 34.
Berinstein et al., Enhancing cancer vaccines with immunomodulators, Vaccine, 2007, B72-B88, 25(Suppl 2).
Ellmark et al., Pre-assembly of the extracellular domains of CD40 is not necessary for rescue of mouse B cells from anti-immunoglobulin M-induced apoptosis, Immunology, 2003, 452-7, 108.
Foy et al., In vivo CD40-gp39 interactions are essential for thymus-dependent humoral immunity. II. Prolonged suppression of the humoral immune response by an antibody to the ligand for CD40, J Exp Med., 1993, 1567-1575, 5.
Gatenby et al., Why do cancers have high aerobi glycolysis? Nature Review Cancer, 2004, 891-899, 4.
Gladue et al., The CD40 agonist antibody CP-870,893 enhances dendritic cell and B-cell activity and promotes anti-tumor efficacy in SCID-hu mice, Cancer Immunol Immunotherapy, 2011, 1009-17, 60(7).
Hussein et al., A phase I multi-dose study of dacetumuzumab (SGN-40, a humananized anti-CD40 monoclonal antibody) in patients with multiple myeloma, 2010, Haematologica, 845-848, 95.
Kai et al., Switching constant domains enhances agonist activities of antibodies to a thrombopoietin receptor, Nature Biotechnology, 2008, 209-211, 26.
Kalbasi et al., CD40 expression by human melanocytic lesions and melanoma cell lines and direct CD40 targeting with the therapeutic anti-CD40 antibody CP-870,893, J Immunother, 2010, 810-816, 33.
Katakura et al., A practical kinetic model for efficient isolation of useful antibodies from phage display libraries, Journal of Molecular Catalysis B: Enzymatic, 2004, 191-200, 28(4-6).
Khalil et al., Anti-CD40 agonist antibodies: preclinical and clinical experience, Update Cancer Ther., 2007, 61-65, 2(2).
Khawli et al., Cytokine, Chemokine, and Co-Stimulatory Fusion Proteins for the Immunotherapy of Solid Tumors, Handb. Exp. Pharmacol., 2008, 291-328, 181.
Law et al., Preclinical Antilymphoma Activity of a Humanized Anti-CD40 Monoclonal Antibody, SGN-40, Cancer Research, 2005, 8331-8338, 65.
Loskog et al., The Janus faces of CD40 in cancer, Semin. Immunol, 2009, 301-307, 21.
Melero et al., Immunostimulatory monoclonal antibodies for cancer therapy, Nat Rev Cancer, 2007, 95-106, 7.
Melief et al., Strategies for Immunotherapy of Cancer, Adv. Immunol., 2000, 235-282, 75.
Melief et al., Cancer Immunotherapy by Dendritic Cells, Immunity, 2008, 372-383, 29.
Mellor et al., Creating immune privilege: active local suppression that benefits friends, but protects foes, Nat Rev Immunol., 2008, 74-80, 8.
Mierlo et al., CD40 stimulation leads to effective therapy of CD40 tumors through induction of strong systemic cytotoxic T lymphocyte immunity, Proc. Natl. Acad. Sci. USA, 2002, 5561-5566, 99.
Neron et al., CD40-activated B cells from patients with systemic lupus erythematosus can be modulated by therapeutic immuno-globulins in vitro, Arch. Immunol. Ther. Exp., 2009, 447-458, 57.
Wilson et al., An Fcg Receptor-Dependent Mechanism Drives Antibody-Mediated Target-Receptor Signaling in Cancer Cells, Cancer Cell, 2011, 101-113, 19.

(56) References Cited

OTHER PUBLICATIONS

Ottaiano et al., CD40 activation as potential tool in malignant neoplasms, Tumori, 2002, 361-366, 88.
Pound et al., Minimal cross-linking and epitope requirements for CD40-dependent suppression of apoptosis contrast with those for promotion of the cell cycle and homotypic adhesions in human B cells, International Immunology, 1999, 11-20, 11(1).
Schonbeck et al., The CD40/CD154 receptor/ligand dyad, Cell. Life. Sci., 2001, 4-43, 58.
Sklar et al., Flow cytometric analysis of ligand-receptor interactions and molecular assemblies, Annual Review Biophysical Biomol Structure, 2002, 97-119, 31.
Soderlind et al., Recombining germline-derived CDR sequences for creating diverse single framework antibody librariesNat Biotechnol, 2000, 852-6, 18.
Sotomayor et al., Conversion of tumor-specific CD4+ T-cell tolerance to T-cell priming through in vivo ligation of CD40, Nature Medicine 1999, 780-787, 5.
Stagg et al., From cancer immunosurveillance to cancer immunotherapy, Immunological Reviews, 2007, 82-101, 220.
Staveley-O'Carroll et al., In Vivo Ligation of CD40 Enhances Priming Against the Endogenous Tumor Antigen and Promotes CD8+ T Cell Effector Function in SV40 T Antigen Transgenic Mice, J Immunol, 2003, 697-707, 171.
Tutt et al., T cell immunity to lymphoma following treatment with anti-CD40 monoclonal antibody, J Immunol, 2002, 2720-2728, 168(6).
Van Mierlo et al., Activation of Dendritic Cells That Cross-Present Tumor-Derived Antigen Licenses CD8 CTL to Cause Tumor Eradication, J Immunol, 2004, 6753-6759, 173.
VonderHeide et al., Clinical Activity and Immune Modulation in Cancer Patients Treated With CP-870,893, a Novel CD40 Agonist Monoclonal Antibody, J Clin Oncol., 2007, 876-83, 25(7).
Waldmann et al., Effective cancer therapy through immunomodulation, Annu Rev Med., 2006, 65-81, 57.
Malmborg Hager, A.C., "Affinity and Epitope Profiling of Mouse Anti-CD40 Monoclonal Antibodies," Scandinavian J. Immunol. (2003) 57:517-524.
VonderHeide, et al., "Agonistic CD40 antibodies and cancer therapy" Clin. Cancer Res. (2013) 19(5): 1035-1043.
Smothers, et al., "AMP-224, A Fusion Protein That Targets PD-1" Annals of Oncology (2013) 24 (Supplement 1):i7.
Shih, et al., "Clinical Impact of Checkpoint Inhibitors as Novel Cancer Therapies" Drugs (2014) 74:1993-2013.
Renaeus, et al., "First-in-human study with intratumoral administration of a CD40 agonistic antibody, ADC-1013, in advanced solid malignancies" Int. J. Cancer (2019) doi: 10.1002/ijc.32141.
Brahmer, et al., "Safety and Activity of Anti-PD-L1 Antibody in Patients with Advanced Cancer", N. Engl. J. Med. (2012) 366:2455-2465.
Miles, et al., "Combination Versus Sequential Single-Agent Therapy in Metastatic Breast Cancer", The Oncologist (2002) 7(suppl 6):13-19.
Topalian, et al., "Safety, Activity, and Immune Correlates of Anti-PD-1 Antibody in Cancer", N. Engl. J. Med. (2012) 366:2443-2454.
Singapore Patent Application No. 11201701070W, "ADC-1013 administered locally or systemically improves survival of MB49 tumor-bearing mice", Intellectual Property Office of Singapore, submitted Nov. 13, 2019, single graph, not the entire document.
Deronic, et al., "The agonistic CD40 antibody ADC-1013 improves T cell responses and delays growth of a syngeneic tumor in an ovalbumin vaccination model," World Preclinical Congress, Jun. 18-21, 2018, Boston, MA.
Calvo, et al., "A Phase 1 Study to Assess Safety, Pharmacokinetics (PK) and Pharmacodynamics (PD) of JNJ-64457107, a CD40 Agonistic Monoclonal Antibody, in Patients (pts) with Advanced Solid Tumors," American Society of Clinical Oncology (ASCO) Annual Meeting, Jun. 4, 2019, Chicago, IL.
Pistoia, et al., "Immunosuppressive microenvironment in neuroblastoma" Frontiers in Oncology (2013) 3:167 (pp. 1-8).
Ascierto, P.A., et al., "Biomarkers for Immunostimulatory Monoclonal Antibodies in Combination Strategies for Melanoma and Other Tumor Types" Clin. Cancer Res. (2013) 19(5):1009-20.
Gilboa, E., et al., "Use of Oligonucleotide Aptamer Ligands to Modulate the Function of Immune Receptors" Clin. Cancer Res. (2013) 19(5): 1054-62.
Melero, I., et al., "Agonist Antibodies to TNFR Molecules that Costimulate T and NK Cells" Clin. Cancer Res. (2013) 19(5):1044-1053.
Melero, I., et al., "Clinical Development of Immunostimulatory Monoclonal Antibodies and Opportunities for Combination" Clin. Cancer Res. (2013) 19(5):997-1008.
Sznol, M., et al., "Antagonist Antibodies to PD-1 and B7-H1 (PD-L1) in the Treatment of Advanced Human Cancer" Clin. Cancer Res. (2013) 19(5):1021-1034.

\* cited by examiner

A

B

SEQUENCE LISTING

```
<160> NUMBER OF SEQ ID NOS: 13

<210> SEQ ID NO 1
<211> LENGTH: 15
<212> TYPE: PRT
<213> ORGANISM: Artificial Sequence
<220> FEATURE:
<223> OTHER INFORMATION: Variable light chain complementarity
      determining region 1

<400> SEQUENCE: 1

Cys Thr Gly Ser Ser Ser Asn Ile Gly Ala Gly Tyr Asn Val Tyr
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Variable light chain complementarity
      determining region 2

<400> SEQUENCE: 2

Gly Asn Ile Asn Arg Pro Ser
1               5

<210> SEQ ID NO 3
<211> LENGTH: 12
<212> TYPE: PRT
<213> ORGANISM: Artificial Sequence
<220> FEATURE:
<223> OTHER INFORMATION: Variable light chain complementarity
      determining region 3

<400> SEQUENCE: 3
```

Cys Ala Ala Trp Asp Lys Ser Ile Ser Gly Leu Val
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Variable heavy chain complementarity
      determining region 1

<400> SEQUENCE: 4

Gly Phe Thr Phe Ser Thr Tyr Gly Met His
1               5                   10

<210> SEQ ID NO 5
<211> LENGTH: 26
<212> TYPE: PRT
<213> ORGANISM: Artificial Sequence
<220> FEATURE:
<223> OTHER INFORMATION: Variable heavy chain complementarity
      determining region 2

<400> SEQUENCE: 5

Gly Lys Gly Leu Glu Trp Leu Ser Tyr Ile Ser Gly Gly Ser Ser Tyr
1               5                   10                  15

Ile Phe Tyr Ala Asp Ser Val Arg Gly Arg
            20                  25

<210> SEQ ID NO 6
<211> LENGTH: 13
<212> TYPE: PRT
<213> ORGANISM: Artificial Sequence
<220> FEATURE:
<223> OTHER INFORMATION: Variable heavy chain complementarity
      determining region 3

<400> SEQUENCE: 6

Cys Ala Arg Ile Leu Arg Gly Gly Ser Gly Met Asp Leu
1               5                   10

<210> SEQ ID NO 7
<211> LENGTH: 112
<212> TYPE: PRT
<213> ORGANISM: Artificial Sequence
<220> FEATURE:
<223> OTHER INFORMATION: Variable light chain amino acid sequence

<400> SEQUENCE: 7

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asn Val Tyr Trp Tyr Gln Gln Leu Pro Gly Thr Ala Pro Lys Leu
        35                  40                  45

Leu Ile Tyr Gly Asn Ile Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Lys Ser
                85                  90                  95

Ile Ser Gly Leu Val Phe Gly Gly Gly Thr Lys Leu Thr Val Leu Gly
            100                 105                 110

<210> SEQ ID NO 8
<211> LENGTH: 119
<212> TYPE: PRT
<213> ORGANISM: Artificial Sequence
<220> FEATURE:
<223> OTHER INFORMATION: Variable heavy chain amino acid sequence

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Leu
        35                  40                  45

Ser Tyr Ile Ser Gly Gly Ser Ser Tyr Ile Phe Tyr Ala Asp Ser Val
    50                  55                  60

Arg Gly Arg Phe Thr Ile Ser Arg Asp Asn Ser Glu Asn Ala Leu Tyr
65                  70                  75                  80

Leu Gln Met Asn Ser Leu Arg Ala Glu Asp Thr Ala Val Tyr Tyr Cys
                85                  90                  95

Ala Arg Ile Leu Arg Gly Gly Ser Gly Met Asp Leu Trp Gly Gln Gly
            100                 105                 110

Thr Leu Val Thr Val Ser Ser
        115

<210> SEQ ID NO 9
<211> LENGTH: 336
<212> TYPE: DNA
<213> ORGANISM: Artificial Sequence
<220> FEATURE:
<221> NAME/KEY: source
<222> LOCATION: 1..336
<223> OTHER INFORMATION: /mol_type="unassigned DNA"
      /note="Variable light chain nucleotide sequence "
      /organism="Artificial Sequence"

<400> SEQUENCE: 9
cagtctgtgc tgactcagcc accctcagcg tctgggaccc ccgggcagag ggtcaccatc      60
tcttgcactg ggagcagctc caacatcggg gcgggttaca atgtatactg gtatcagcag     120
ctcccaggaa cggcccccaa actcctcatc tatggtaaca tcaatcggcc ctcaggggtc     180
cctgaccgat tctctggctc caagtctggc acctcagcct ccctggccat cagtgggctc     240
cggtccgagg atgaggctga ttattactgt gcagcatggg ataagagcat ttctggtctg     300
gttttcggcg gaggaaccaa gctgacggtc ctaggt                                336

<210> SEQ ID NO 10
<211> LENGTH: 357
<212> TYPE: DNA
<213> ORGANISM: Artificial Sequence
<220> FEATURE:
<221> NAME/KEY: source
<222> LOCATION: 1..357
<223> OTHER INFORMATION: /mol_type="unassigned DNA"
      /note="Variable heavy chain nucleotide sequence"
      /organism="Artificial Sequence"

<400> SEQUENCE: 10
gaggtgcagc tgttggagtc tgggggaggc ttggtacagc ctggggggtc cctgagactc      60
tcctgtgcag cctctggatt caccttcagt acttatggca tgcactgggt ccgccaggct     120
ccagggaagg ggctggagtg gctttcatat attagtggtg gtagtagtta catttttctac     180

```
gcagactcag tgaggggccg attcaccatc tccagagaca actccgagaa cgcgctgtat    240
ctgcaaatga acagcctgag agccgaggac acggccgtgt attactgtgc gagaatatta    300
agaggcggga gcggtatgga cctctggggc caaggtacac tggtcaccgt gagctca       357
```

```
<210> SEQ ID NO 11
<211> LENGTH: 105
<212> TYPE: PRT
<213> ORGANISM: Homo sapiens
<220> FEATURE:
<223> OTHER INFORMATION: Human Ig lambda light chain C2 region

<400> SEQUENCE: 11

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105
```

```
<210> SEQ ID NO 12
<211> LENGTH: 330
<212> TYPE: PRT
<213> ORGANISM: Homo sapiens
<220> FEATURE:
<223> OTHER INFORMATION: Human Ig gamma-1 heavy chain constant region

<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
                165                 170                 175
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 13
<211> LENGTH: 277
<212> TYPE: PRT
<213> ORGANISM: Homo sapiens
<220> FEATURE:
<223> OTHER INFORMATION: Human CD40 sequence

<400> SEQUENCE: 13

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
```

```
              195                 200                 205
Leu Leu Val Leu Val Phe Ile Lys Lys Val Ala Lys Lys Pro Thr Asn
        210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
                260                 265                 270

Val Gln Glu Arg Gln
        275
```

COMBINATION THERAPIES WITH ANTI CD40 ANTIBODIES

This application is a § 371 application of PCT/EP2015/068598, filed Aug. 12, 2015, which in turn claims priority to GB Application 1414270.7, filed Aug. 12, 2014; GB Application 1422614.6, filed Dec. 18, 2014; and GB Application 1507541.9, filed May 1, 2015. The entire disclosure of each of the foregoing applications is incorporated by reference herein.

FIELD OF THE INVENTION

The present invention relates to combination therapies for treating a solid tumour in a subject, as well as methods for use thereof. The combination therapies comprise (a) an antibody, or antigen-binding fragment thereof, that specifically binds to CD40 and (b) a further immunotherapeutic agent that specifically binds to an immune checkpoint molecule other than CD40. The invention also relates to a kit and methods of using the combination therapies of the invention.

BACKGROUND TO THE INVENTION

Cancer is a leading cause of premature deaths in the developed world. The aim of immunotherapy in cancer is to mount an effective immune response by the body against a tumour, particularly a solid tumour. This may be achieved by, for example, breaking tolerance against tumour antigen, augmenting anti-tumor immune responses, and stimulating local cytokine responses at the tumor site. The key effector cell of a long lasting anti-tumor immune response is the activated tumor specific effector T cell. Incomplete activation of effector T cells by, for example, dendritic cells can cause T-cell anergy, which results in an inefficient anti-tumor response, whereas adequate induction by dendritic cells can generate a potent expansion of activated effector T cells, redirecting the immune response towards the tumor.

The cell surface CD40 receptor molecule is a member of the tumour necrosis factor receptor superfamily (TNFR) and is a key regulator in both innate and adaptive immune responses. It is expressed on human antigen presenting cells, in particular B cells, dendritic cells and macrophages, as well as on normal cells, such as fibroblasts, smooth muscle cells, endothelial cells and epithelial cells. Moreover, it is expressed on a wide range of tumor cells, including all B-lymphomas, 30-70% of solid tumours, melanomas and carcinomas.

The natural ligand of CD40, designated CD154 or CD40L, is mainly expressed on mature T lymphocytes. CD40L-mediated signalling triggers several biological events, including immune cell activation, proliferation, and production of cytokines and chemokines. Thus, stimulation via the CD40 receptor enhances cellular and immune functions. Its role in cell-mediated immune responses is well known. For example, the activation of dendritic cells via CD40 stimulation, induces activation of effector T cells. Treatment with CD40 agonists may thus provide the means to redirect the immune response and expand effector T cells directed to tumour Antitumour effects have been reported for some anti-CD40 antibodies, with several mechanisms having been identified. An indirect effect is observed for CD40 negative tumors, involving the activation of antigen presenting cells, in particular increased activity by tumor specific cytotoxic T lymphocytes and natural killer cells (NK cells). Both indirect and direct antitumor mechanisms are observed for CD40 positive tumours, wherein the CD40 antibody binding to tumour cells induces cell apoptosis. These mechanisms for anti-tumour activity may be complemented by antibody mediated cellular cytotoxicity (ADCC). However, administration of anti-CD40 antibodies has also been associated with adverse side effects, such as cytokine release syndrome.

Accordingly there remains a need for improved cancer therapies, in particular anti-CD40 antibodies suitable for use in treating solid tumours and combination therapies thereof.

SUMMARY OF THE INVENTION

A first aspect of the invention provides a combination therapy for use in treating a solid tumour in a subject comprising (a) an antibody, or antigen-binding portion thereof, that specifically binds to CD40, and (b) a further immunotherapeutic agent with efficacy in the treatment of cancer, which agent is not an anti-CD40 antibody or antigen-binding fragment thereof, wherein the antibody or antigen-binding portion thereof that specifically binds to CD40 competes for binding to human CD40 with an antibody which comprises the light chain variable region of SEQ ID NO: 7 and the heavy chain variable region of SEQ ID NO: 8, and wherein the further immunotherapeutic agent specifically binds to an immune checkpoint molecule other than CD40.

In one embodiment, the solid tumour is selected from the groups consisting of an adenoma, a blastoma, a carcinoma, a desmoid tumour, a desmopolastic small round cell tumour, an endocrine tumour, a germ cell tumour, a lymphoma, a sarcoma, a Wilms tumour, a lung tumour, a colon tumour, a lymph tumour, a breast tumour and a melanoma. For example, the solid tumour may be a melanoma, such as a metastatic melanoma.

In one embodiment, the antibody or antigen-binding portion thereof that specifically binds to CD40 comprises or consists of an intact antibody.

In an alternative embodiment, the antibody or antigen-binding portion thereof that specifically binds to CD40 comprises or consists of an antigen-binding fragment selected from the group consisting of: an Fv fragment (such as a single chain Fv fragment, or a disulphide-bonded Fv fragment), and a Fab-like fragment (such as a Fab fragment; a Fab' fragment or a F(ab)$_2$ fragment).

In one embodiment, the antibody or antigen-binding portion thereof is human or humanised.

In one embodiment, the antibody or antigen-binding portion thereof that specifically binds to CD40 comprises at least one CDR selected from SEQ ID NOs 1, 2, 3, 4, 5 and 6, or a 'core' CDR sequence thereof (see Example 1 below for sequence details).

Thus, the antibody or antigen-binding portion thereof that specifically binds to CD40 comprises the CDR sequences of SEQ ID NOs: 1, 2 and 3 and/or SEQ ID NOs: 4, 5 and 6, or a 'core' CDR sequence thereof.

For example, the antibody or antigen-binding portion thereof that specifically binds to CD40 comprises the light chain variable region of SEQ ID NO: 7 and/or the heavy chain variable region of SEQ ID NO: 8.

In one embodiment, the antibody or antigen-binding portion thereof that specifically binds to CD40 comprises the light chain constant region of SEQ ID NO: 11 and/or the heavy chain constant region of SEQ ID NO: 12.

Thus, the antibody or antigen-binding portion thereof that specifically binds to CD40 comprises or consists of the light chain of SEQ ID NO: 7 plus SEQ ID NO:11, and/or the heavy chain of SEQ ID NO: 8 plus SEQ ID NO:12.

The combination therapies of the invention additionally comprise a further immunotherapeutic agent, effective in the treatment of cancer, that specifically binds to an immune checkpoint molecule other than CD40. It will be appreciated that the therapeutic benefit of the further immunotherapeutic agent may be mediated by attenuating the function of an inhibitory immune checkpoint molecule and/or by activating the function of a stimulatory immune checkpoint molecule.

In another embodiment, the further immunotherapeutic agent is selected from the groups consisting of:
(a) an immunotherapeutic agent that binds PD-1;
(b) an immunotherapeutic agent that binds CTLA-4;
(c) an immunotherapeutic agent that binds OX40; and
(d) an immunotherapeutic agent that binds CD137.

Thus, the further immunotherapeutic agent may be a PD1 inhibitor, such as an anti-PD1 antibody, or antigen-binding fragment thereof capable of inhibiting PD1 function (for example, Nivolumab, Pembrolizumab, Lambrolizumab, Pidilzumab and AMP-224). Alternatively, the PD1 inhibitor may comprise or consist of an anti-PD-L1 antibody, or antigen-binding fragment thereof capable of inhibiting PD1 function (for example, MEDI-4736 and MPDL3280A).

In another embodiment, the further immunotherapeutic agent is a CTLA-4 inhibitor, such as an anti-CTLA-4 antibody or antigen-binding portion thereof.

In a further embodiment, the further immunotherapeutic agent activates OX40, such as an agonistic anti-OX40 antibody or antigen-binding portion thereof.

In a still further embodiment, the further immunotherapeutic agent activates CD137, such as an agonistic anti-CD137 antibody or antigen-binding portion thereof It will be appreciated by persons skilled in the art that the presence of the two active agents (as detailed above) may provide a synergistic benefit in the treatment of a solid tumour in a subject. By "synergistic" we include that the therapeutic effect of the two agents in combination (e.g. as determined by reference to the rate of growth or the size of the tumour) is greater than the additive therapeutic effect of the two agents administered on their own. Such synergism can be identified by testing the active agents, alone and in combination, in a relevant cell line model of the solid tumour.

Optionally, the combination therapy further comprises a third immunotherapeutic agent with efficacy in the treatment of cancer.

For example, the combination therapy may comprise (a) an antibody, or antigen-binding portion thereof, that specifically binds to CD40, (b) an antibody, or antigen-binding portion thereof, that specifically binds to PD1 or PD-L1, and (c) an antibody, or antigen-binding portion thereof, that specifically binds to CTLA-4.

A second aspect of the invention provides an antibody, or antigen-binding portion thereof, that specifically binds to CD40 for use in a method of treating a solid tumour, wherein the antibody or antigen-binding portion thereof that specifically binds to CD40 competes for binding to human CD40 with an antibody which comprises the light chain variable region of SEQ ID NO: 7 and the heavy chain variable region of SEQ ID NO: 8, and wherein the antibody or antigen-binding portion thereof that specifically binds to CD40 is for use in combination with a further immunotherapeutic agent with efficacy in the treatment of cancer, which agent is not an anti-CD40 antibody or antigen-binding fragment thereof.

In one embodiment, the antibody or antigen-binding portion thereof that specifically binds to CD40 is as discussed above in relation to the first aspect of the invention.

In one embodiment, the further immunotherapeutic agent with efficacy in the treatment of cancer is as discussed above in relation to the first aspect of the invention.

A related, third aspect of the invention provides the use of an antibody, or antigen-binding portion thereof, that specifically binds to CD40 in the preparation of a medicament for treating a solid tumour, wherein the antibody or antigen-binding portion thereof that specifically binds to CD40 competes for binding to human CD40 with an antibody which comprises the light chain variable region of SEQ ID NO: 7 and the heavy chain variable region of SEQ ID NO: 8, and wherein the antibody or antigen-binding portion thereof that specifically binds to CD40 is for use in combination with a further immunotherapeutic agent with efficacy in the treatment of cancer, which agent is not an anti-CD40 antibody or antigen-binding fragment thereof.

In one embodiment, the antibody or antigen-binding portion thereof that specifically binds to CD40 is as discussed above in relation to the first aspect of the invention.

In one embodiment, the further immunotherapeutic agent with efficacy in the treatment of cancer is as discussed above in relation to the first aspect of the invention.

A fourth aspect of the invention provides a pharmaceutical composition comprising (a) an antibody, or antigen-binding portion thereof, that specifically binds to CD40, and (b) a further immunotherapeutic agent with efficacy in the treatment of cancer, which agent is not an anti-CD40 antibody or antigen-binding fragment thereof, wherein the antibody or antigen-binding portion thereof that specifically binds to CD40 competes for binding to human CD40 with an antibody which comprises the light chain variable region of SEQ ID NO: 7 and the heavy chain variable region of SEQ ID NO: 8.

In one embodiment, the antibody or antigen-binding portion thereof that specifically binds to CD40 is as discussed above in relation to the first aspect of the invention.

In one embodiment, the further immunotherapeutic agent with efficacy in the treatment of cancer is as discussed above in relation to the first aspect of the invention.

A fifth aspect of the invention provides a kit for treating a solid tumour comprising (a) an antibody, or antigen-binding portion thereof, that specifically binds to CD40, and (b) a further immunotherapeutic agent with efficacy in the treatment of cancer, which agent is not an anti-CD40 antibody or antigen-binding fragment thereof, wherein the antibody or antigen-binding portion thereof that specifically binds to CD40 competes for binding to human CD40 with an antibody which comprises the light chain variable region of SEQ ID NO: 7 and the heavy chain variable region of SEQ ID NO: 8.

In one embodiment, the antibody or antigen-binding portion thereof that specifically binds to CD40 is as discussed above in relation to the first aspect of the invention.

In one embodiment, the further immunotherapeutic agent with efficacy in the treatment of cancer is as discussed above in relation to the first aspect of the invention.

A sixth aspect of the invention provides a method for treating a solid tumour in a subject, the method comprising administering to the subject a therapeutically effect amount of (a) administering to the subject a therapeutically effect amount of an antibody, or antigen-binding portion thereof, that specifically binds to CD40, and (b) administering to the subject a therapeutically effect amount of a further immunotherapeutic agent with efficacy in the treatment of cancer, which agent is not an anti-CD40 antibody or antigen-binding fragment thereof, wherein the antibody or antigen-binding portion thereof that specifically binds to CD40 competes for binding to human CD40 with an antibody which comprises the light chain variable region of SEQ ID NO: 7 and the heavy chain variable region of SEQ ID NO: 8.

In one embodiment, the antibody or antigen-binding portion thereof that specifically binds to CD40 is as discussed above in relation to the first aspect of the invention.

In one embodiment, the further immunotherapeutic agent with efficacy in the treatment of cancer is as discussed above in relation to the first aspect of the invention.

In a further embodiment, steps (a) and (b) are carried out simultaneously or wherein step (b) is carried out between 24 hours and two weeks after step (a), between 24 hours and one week after step (a), between 24 and 72 hours after step (a), or between 24 and 48 hours after step (a).

In one embodiment, step (a) comprises local administration of the antibody to the tumour site.

In one embodiment, at least 30% of the amount of antibody administered in step (a) is retained at the tumour site at four hours after administration, preferably wherein at least 40% of the said amount is retained at the tumour site at four hours after administration.

In one embodiment, the additional therapeutic agent of step (b) is formulated as a composition suitable for systemic administration with at least one pharmaceutically acceptable diluent or carrier.

In one embodiment, step (a) is conducted on multiple separate occasions and step (b) is conducted such that exposure of the subject to the additional therapeutic agent is continuous for the duration of the method.

In one embodiment, the subject is a human.

The inventors have also surprisingly shown that certain anti-CD40 antibodies are retained at the site of a solid tumour after administration to a subject. Thus, only a small proportion of the antibody escapes from the tumour site into the vascular or lymphatic circulation of the subject.

This results in a highly effective treatment, as well as reduced side-effects, enabling a lower dose of antibody to be used. These advantages are particularly apparent when such an antibody is locally administered to a tumour site in a subject, but may also be apparent when the antibody is systemically administered.

However, it will be appreciated by persons skilled in that art that the anti-CD40 antibody may also be administered to the subject systemically, e.g. intravenous or sub-cutaneous.

The inventors have also surprisingly shown that combining administration of an anti-CD40 antibody which is retained at the tumour site with the systemic administration to a subject of an additional therapeutic agent results in an improvement in the treatment effect, relative to the administration of the anti-CD40 antibody alone.

The invention therefore provides a method for treating a solid tumour in a subject, the method comprising (a) administering to the subject a therapeutically effective amount of an antibody that specifically binds to CD40 and that is retained at the tumour site following administration, and optionally (b) systemically administering to the subject a therapeutically effective amount of an additional therapeutic agent. Steps (a) and (b) may be carried out simultaneously. Alternatively steps (a) and (b) may be carried our sequentially provided step (a) precedes step (b). In step (a), the anti-CD40 antibody is preferably administered locally to the tumour.

The invention also provides a kit for treating a solid tumour in a subject, the kit comprising (a) a therapeutically effective amount of an antibody that specifically binds to CD40 and that is retained at the tumour site following administration and optionally (b) a therapeutically effective amount of an additional therapeutic agent that is suitable for systemic administration to a subject. The antibody that specifically binds to CD40 is preferably provided in a form suitable for local administration to a tumour.

BRIEF DESCRIPTION OF THE SEQUENCE LISTING

SEQ ID NO: 1, 2 and 3 are CDRs 1, 2 and 3 respectively of the light chain of the antibody G12 (defined in accordance with IMGT numbering).
SEQ ID NO: 4, 5 and 6 are the CDRs 1, 2 and 3 respectively of the heavy chain of the antibody G12 (defined in accordance with IMGT numbering).
SEQ ID NO: 7 and 8 are the amino acid sequences of the light chain variable region and the heavy chain variable region, respectively, of the antibody G12.
SEQ ID NO: 9 and 10 are the nucleic acid sequences of the light chain variable region and the heavy chain variable region, respectively, of the antibody G12.
SEQ ID NO: 11 is the amino acid sequence of an exemplary light chain constant region.
SEQ ID NO: 12 is the amino acid sequence of an exemplary heavy chain constant region.
SEQ ID NO: 13 is the amino acid sequence of human CD40.

BRIEF DESCRIPTION OF THE FIGURES

FIG. 4 (bottom panel) shows tumour volume for each treatment group at the day when the first mouse was sacrificed. The graphs show pooled data from two individual experiments (n=16). Significant anti-tumor efficacy and increased survival was demonstrated with ADC-1013 treatment. Improved anti-tumor efficacy and improved survival was observed with combined treatment with anti-PD-1 (*=p<0.05, **=<0.01, Log rank test for the survival and Mann-Whitney test for tumor volume).

DETAILED DESCRIPTION OF THE INVENTION

Figure 1:
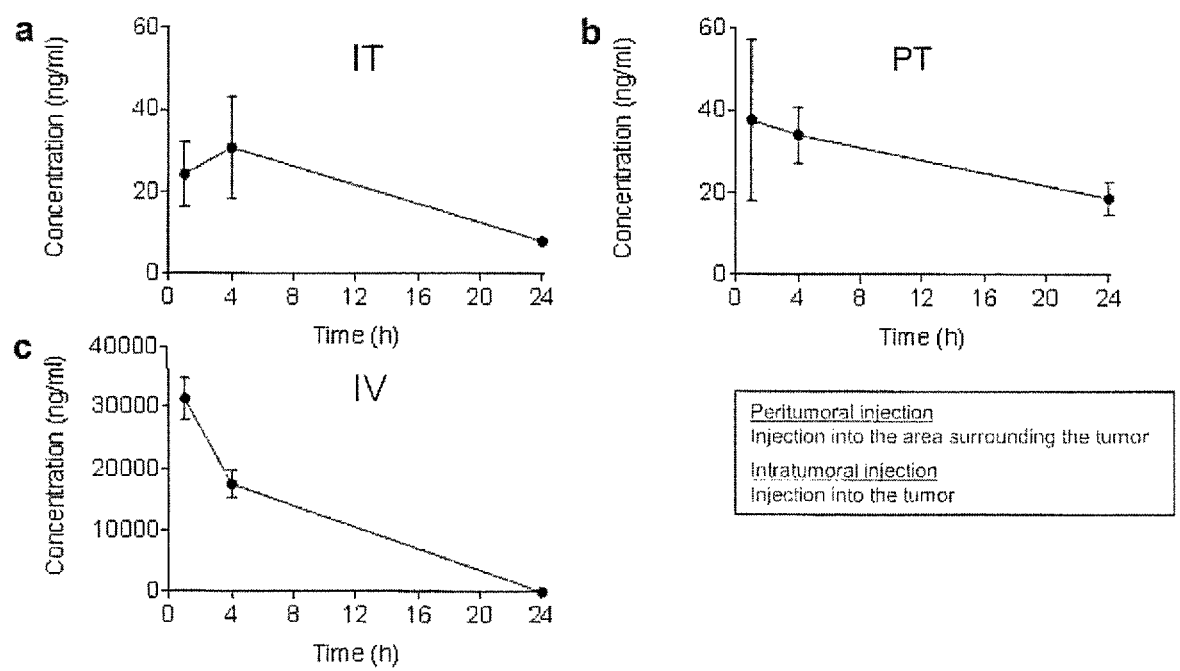
FIG. 1 shows the level of antibody detectable in serum of hCD40tg mice bearing a tumour of hCD40 negative bladder cancer cells MB49, after administration of antibody (a) intratumorally (IT), (b) peritumorally (PT) or (c) intravenously (IV) at a dose of 100 μg.

It is to be understood that different applications of the disclosed combination therapies and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "an antibody" includes "antibodies", reference to "an antigen" includes two or more such antigens, reference to "a subject" includes two or more such subjects, and the like.

A "polypeptide" is used herein in its broadest sense to refer to a compound of two or more subunit amino acids, amino acid analogs, or other peptidomimetics. The term "polypeptide" thus includes short peptide sequences and also longer polypeptides and proteins. As used herein, the term "amino acid" refers to either natural and/or unnatural or synthetic amino acids, including glycine and both the D or L optical isomers, and amino acid analogs and peptidomimetics.

By "retained at the site of a solid tumour" we include that the anti-CD40 antibody is released only slowly from the tumour area. Retention of the antibody at the tumour site may be assessed by monitoring serum levels of the antibody post-administration (see Mangsbo et al., 2014, Clin. Cancer Res. 21(5):1115-1126, the disclosure of which are incorporated herein by reference). For example, in one embodiment, the serum levels of anti-CD40 four hours following intratumoral injection of 30 µg of the antibody (in 60 µL) are less than 1 µL/ml.

By "therapeutically effective amount" of a substance, it is meant that a given substance is administered to a subject suffering from a condition, in an amount sufficient to cure, alleviate or partially arrest the condition or one or more of its symptoms. Such therapeutic treatment may result in a decrease in severity of disease symptoms, or an increase in frequency or duration of symptom-free periods. Effective amounts for a given purpose and a given agent will depend on the severity of the disease or injury as well as the weight and general state of the subject. As used herein, the term "subject" includes any mammal, preferably a human.

All publications, patents and patent applications cited herein, whether supra or infra, are hereby incorporated by reference in their entirety.

Methods

The invention provides a method for treating a solid tumour in a subject. The tumour is typically malignant and may be metastatic.

Solid tumours are classically defined by the tissue from which they originate, e.g. breast, colon etc. However, since immunotherapy acts on the immune system, and not the tumour itself, the immune status of the tumour may be more predictive of the response than the origin of the tumour. In the supporting studies presented herein, two different models in more detail, a melanoma model, B16.F10 (with and without human CD40) and the MB49 bladder tumor model. The data presented in the Examples below show that MB49 is more immunogenic than B16.F10. However, in both models a significant anti-tumour effect is observed following treatment with an anti-CD40 antibody as described herein. Thus, the invention provides an anti-tumour effect both in immunogenic tumours (such MB49) and poorly immunogenic models (such B16.F10).

Thus, in one embodiment of the present invention, the tumour is immunogenic. Such tumours are characterised by infiltration of immune cells, such as T cells and cells of myeloid origin. It has been demonstrated that infiltration of CD8 T cells, i.e. a more immunogenic tumour profile, correlates with a good prognosis following therapy, for example in colon cancer, (Galon et al., 2014, J. Pathol. 232(2):199-209).

In an alternative embodiment of the invention, the tumour is non-immunogenic or poorly-immunogenic. Poorly immunogenic tumours often have low or absent MHCI expression and are characterized by lower number of infiltrating immune cells, such as T cells and cells of myeloid origin (Lechner et al., 2013, J Immunotherapy 36(9):477-89).The tumour may be an adenoma, an adenocarcinoma, a blastoma, a carcinoma, a desmoid tumour, a desmoplastic small round cell tumour, an endocrine tumour, a germ cell tumour, a lymphoma, a sarcoma, a Wilms tumour, a lung tumour, a colon tumour, a lymph tumour, a breast tumour or a melanoma.

Types of blastoma include hepatblastoma, glioblastoma, neuroblastoma or retinoblastoma. Types of carcinoma include colorectal carcinoma or heptacellular carcinoma, pancreatic, prostate, gastric, esophegal, cervical, and head and neck carcinomas, and adenocarcinoma. Types of sarcoma include Ewing sarcoma, osteosarcoma, rhabdomyosarcoma, or any other soft tissue sarcoma. Types of melanoma include Lentigo maligna, Lentigo maligna melanoma, Superficial spreading melanoma, Acral lentiginous melanoma, Mucosal melanoma, Nodular melanoma, Polypoid melanoma, Desmoplastic melanoma, Amelanotic melanoma, Soft-tissue melanoma, Melanoma with small nevus-like cells, Melanoma with features of a Spitz nevus and Uveal melanoma. Types of lymphoma include Precursor T-cell leukemia/lymphoma, Follicular lymphoma, Diffuse large B cell lymphoma, Mantle cell lymphoma, B-cell chronic lymphocytic leukemia/lymphoma, MALT lymphoma, Burkitt's lymphoma, Mycosis fungoides, Peripheral T-cell lymphoma, Nodular sclerosis form of Hodgkin lymphoma, Mixed-cellularity subtype of Hodgkin lymphoma. Types of lung tumour include tumours of non-small-cell lung cancer (adenocarcinoma, squamous-cell carcinoma and large-cell carcinoma) and small-cell lung carcinoma.

There is an increasing incidence of melanoma and approximately 200,000 new cases are diagnosed world wide each year. Furthermore, melanoma is very well suited for local administration in the clinic since both the primary tumors as well as metastases are often easily accessible. Thus, for the method of the invention, the tumour is preferably a melanoma, and is most preferably a metastatic melanoma. The tumour may have been classified as metastatic due to a high lactate dehydrogenase test result. The tumour may have been classified as any one of the following Stages, but is preferably stage III or IV.

Stage 0: Melanoma in situ (Clark Level I), 99.9% survival
Stage I/II: Invasive melanoma, 89-95% survival
T1a: Less than 1.0 mm primary tumor thickness, without ulceration, and mitosis<1/mm$^2$
T1b: Less than 1.0 mm primary tumor thickness, with ulceration or mitoses≥1/mm$^2$
T2a: 1.01-2.0 mm primary tumor thickness, without ulceration
Stage II: High risk melanoma, 45-79% survival
T2b: 1.01-2.0 mm primary tumor thickness, with ulceration
T3a: 2.01-4.0 mm primary tumor thickness, without ulceration
T3b: 2.01-4.0 mm primary tumor thickness, with ulceration
T4a: Greater than 4.0 mm primary tumor thickness, without ulceration
T4b: Greater than 4.0 mm primary tumor thickness, with ulceration
Stage III: Regional metastasis, 24-70% survival
N1: Single positive lymph node
N2: Two to three positive lymph nodes or regional skin/in-transit metastasis
N3: Four positive lymph nodes or one lymph node and regional skin/in-transit metastases
Stage IV: Distant metastasis, 7-19% survival
M1a: Distant skin metastasis, normal LDH
M1b: Lung metastasis, normal LDH
M1c: Other distant metastasis or any distant metastasis with elevated LDH The method of the invention comprises (a) administering to the subject a therapeutically effective amount of an antibody that specifically binds to CD40 and that is retained at the tumour site following administration, and optionally (b) systemically administering to the subject a therapeutically effective amount of an additional therapeutic agent. Retention of an antibody at a tumour site is described in more detail below. Steps (a) and (b) may be carried out simultaneously. Alternatively steps (a) and (b) may be carried our sequentially provided step (a) precedes step (b). In step (a), the anti-CD40 antibody is preferably administered locally to the tumour.

The method of the invention has several advantages. First, because the anti-CD40 antibody is retained at the tumour site, it is highly effective as a treatment. Furthermore, there is reduced systemic exposure to anti-CD40 antibodies, allowing a lower dose of antibody to be used and resulting in fewer side-effects. When step (b) is carried out the treatment effect is further improved.

The invention also provides:

an antibody that specifically binds to CD40 and that is retained at the tumour site following administration for use in a method for treating a solid tumour in a subject, the method comprising (a) administering to the subject a therapeutically effective amount of said antibody that specifically binds to CD40, and optionally (b) systemically administering to the subject a therapeutically effective amount of an additional therapeutic agent. Steps (a) and (b) may be carried out simultaneously. Alternatively steps (a) and (b) may be carried our sequentially provided step (a) precedes step (b). In step (a), said anti-CD40 antibody is preferably administered locally to the tumour.

use of an antibody that specifically binds to CD40 and that is retained at the tumour site following administration in the manufacture of a medicament for treating a solid tumour in a subject, wherein said treating comprises (a) administering to the tumour a therapeutically effective amount of said antibody that specifically binds to CD40, and optionally (b) systemically administering to the subject a therapeutically effective amount of an additional therapeutic agent. Steps (a) and (b) may be carried out simultaneously. Alternatively steps (a) and (b) may be carried our sequentially provided step (a) precedes step (b). In step (a), said anti-CD40 antibody is preferably administered locally to the tumour.

a product containing (1) an antibody that specifically binds to CD40 and that is retained at the tumour site following administration and optionally (2) an additional therapeutic agent for simultaneous, separate or sequential use in a method for treating a solid tumour in a subject, the method comprising (a) locally administering to the tumour a therapeutically effective amount of said antibody that specifically binds to CD40, and optionally (b) systemically administering to the subject a therapeutically effective amount of an additional therapeutic agent. Steps (a) and (b) may be carried out simultaneously. Alternatively steps (a) and (b) may be carried our sequentially provided step (a) precedes step (b). In step (a), said anti-CD40 antibody is preferably administered locally to the tumour.

Timing and Order of Steps (a) and (b)

Steps (a) and (b) are preferably carried out sequentially (i.e. at different times), with step (a) being carried out before step (b).

Steps (a) and (b) are preferably separated by an interval such that the combined anti-tumour effect is optimised. This typically means that step (b) is conducted a sufficiently long interval after step (a) that at least one physiological effect of step (a) is at or close to its peak level. For example, the anti-CD40 antibody will typically stimulate dendritic cells which in turn leads to activation of tumor-specific T cells. The activated T cells begin to express higher levels of immune system checkpoint molecules (such as PD-1) within around 24 hours of treatment with anti-CD40. These immune system checkpoint molecules may negatively regulate the anti-tumour response. The agent administered in step (b) may thus preferably be an agent (such as an anti-PD1 or anti-PDL1 antibody) which blocks or inhibits such the activity of such an immune system checkpoint. Where the agent administered in step (b) is such an agent, step (b) is preferably carried out a sufficiently long interval after step (a) such that the expression level of the immune system checkpoint molecule in cells in the subject, or the number of cells in the subject expressing said immune system checkpoint molecule, is elevated relative to said level or number in the subject prior to step (a), or relative to said level or number in in a healthy subject. In this context, step (b) is preferably conducted between 24 hours and two weeks after step (a), between 24 hours and one week after step (a), between 24 hours and 72 hours after step (a), or between 24 hours and 48 hours after step (a).

Alternatively step (b) may be conducted at a time point after step (a) where the expression level of the immune system checkpoint molecule in a cell of the subject, or the to number of cells in the subject expressing said immune system checkpoint molecule, is determined to be elevated relative to said level or number in the subject prior to step (a), or relative to said level or number in in a healthy subject.

The expression level of an immune system checkpoint molecule in a cell of a subject, or the number of cells in a subject expressing such a molecule, may be determined by any suitable means, for example by flow cytometric analysis of a sample taken from the subject.

Alternatively, it may be preferable to carry out steps (a) and (b) simultaneously (i.e. at the same time), or within 24 hours of each other, such that both steps may be carried out on the same day or during the same visit to a treatment centre. This may be particularly advantageous where access to treatment centres is restricted. In this context, steps (a) and (b) may be carried out simultaneously, or may be carried out less than 24 hours apart, less than 12 hours apart, less than 10 hours apart, less than 6 hours apart, less than 4 hours apart, less than 3 hours apart or less than 2 hours apart.

In any of the above embodiments, step (a) may be conducted on multiple further instances after the first instance. That is, the subject may receive a series of doses of anti-CD40 antibody. These doses are administered such that the subject has only intermittent exposure to the anti-CD40 antibody, preferably such that the immune cells of the subject do not become depleted and/or that the subject does not suffer from tachyphylaxis to the anti-CD40 antibody. At detection of either of these symptoms, the next administration of anti-CD40 antibody may be delayed or cancelled. If multiple doses of anti-CD40 are administered, step (b) is preferably conducted in a manner which, following initiation of step (b), permits continuous exposure of the subject to the additional therapeutic agent for the duration of the method, including during any second and further instances of step (a). This may be particularly appropriate where the additional agent is an agent (such as an anti-PD1 or anti-PDL1 antibody) which blocks or inhibits such the activity of an immune system checkpoint. Continuous receptor blockade may be particularly important for the therapeutic effects of such agents.

Step (a)

Step (a) of the method concerns the local or systemic administration of an anti-CD40 antibody to a subject having a solid tumour. Local administration to the tumour site is preferred and includes peritumoral, juxtatumoral, intratumoral, intralesional, perilesional, intracranial and intravesicle administration by any suitable means, such as injection. Local administration may also include intra cavity infusion and inhalation, depending on the site of the tumour.

A high proportion of the anti-CD40 antibody will be retained at the tumour site in vivo, that is within the tumour microenvironment, for an extended period of time following administration of said antibody. That is, the antibody exhibits reduced leakage from the tumour site into vascular or lymphatic circulation, particularly when locally administered to the tumour site. Preferably at least 30% of an antibody dose administered to a tumour in accordance with the method is retained in the tumour site at four hours after administration, more preferably at least 40% of the dose is retained at four hours after administration and most preferably at least 50% of the dose is retained at four hours after administration.

Antibody retention in a tumour microenvironment can be studied by injecting the antibody into tumours in murine models and measuring the serum levels of the antibody over time after administration. Alternatively the distribution of an antibody can be measured using radiolabeled antibodies injected into tumors in murine models. Suitable techniques are described in the Examples.

The pH in a tumour microenvironment in vivo is significantly more acidic than that of healthy tissues. Ranges for tumours are reported as around pH 6.5 to 7.2 or 6.6 to 7.0, as compared to 7.2 to 7.4 for healthy tissues. This acidity is primarily due to anaerobic glycolysis in tumor regions subjected to short-term or long-term hypoxia as a result of poorly organized vasculature with diminished chaotic blood flow, and aerobic glycolysis (the Warburg effect), a common cancer phenotypic property in which the glycolytic metabolic pathways are used even in the presence of oxygen. Given this acidity, an anti-CD40 antibody used in the method of the invention may preferably have a high isoelectric point because this will lead to improved retention in the tumour microenvironment relative to a similar antibody with a lower isoelectric point.

Isoelectric point of an antibody may be determined by any suitable method. It may be determined in vitro, for example by electrophoretic methods. Alternatively, isoelectric point may be calculated from basic principles. In this case the resulting isoelectric point is typically referred to as a theoretical isoelectric point. Numerous software programs exist for the in silico calculation of theoretical isoelectric point, for example GP-MAW (version 9.2, from Lighthouse Data). An anti-CD40 antibody used in the method of the invention preferably has a theoretical isoelectric point (pI) of 9.0 or above, preferably 9.1 or above, more preferably 9.2 or above, or 9.25 or above, most preferably 9.3 or above.

Step (b)

Step (b) of the method concerns the systemic administration of an additional therapeutic agent to a subject. Systemic administration of any agent described herein (including the anti-CD40 antibody of step (a)) means administration into the circulatory system of the subject, including the vascular and/or lymphatic system. Such administration may be by any suitable route, but is typically parenteral.

The phrase "parenteral administration" as used herein means modes of administration other than enteral and topical administration, and is typically achieved by injection, infusion or implantation. Suitable routes include intravenous, intramuscular, intradermal, intraperitoneal, subcutaneous, spinal, intracerebral, intrathecal, intraosseous or other parenteral routes of administration.

Antibodies
General

The term "antibody" as referred to herein includes whole antibodies and any antigen binding fragment (i.e., "antigen-binding portion") or single chains thereof. An antibody refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region (abbreviated herein as VL) and a light chain constant region. The variable regions of the heavy and light chains contain a binding domain that interacts with an antigen. The VH and VL regions can be further subdivided into regions of hypervariability, termed complementarity determining regions (CDR), interspersed with regions that are more conserved, termed framework regions (FR). The constant regions of the antibodies may mediate the binding of the immunoglobulin to host tissues or factors, including various cells of the immune system (e.g., effector cells) and the first component (Clq) of the classical complement system.

Heavy chains can be of any isotype, including IgG (IgG1, IgG2, IgG3 and IgG4 subtypes), IgA (IgA1 and IgA2 subtypes), IgM and IgE.

Light chains include kappa chains and lambda chains.

Of particular relevance are antibodies and their antigen-binding fragments that have been "isolated" so as to exist in a physical milieu distinct from that in which it may occur in nature or that have been modified so as to differ from a naturally occurring antibody in amino acid sequence An antibody may be a polyclonal antibody or a monoclonal antibody. The antibody may be produced by any suitable method. For example suitable methods for producing monoclonal antibodies are disclosed in "Monoclonal Antibodies; A manual of techniques", H Zola (CRC Press, 1988) and in "Monoclonal Hybridoma Antibodies: Techniques and Application", S G R Hurrell (CRC Press, 1982). Recombinant techniques may also be used.

The term "antigen-binding portion" or "antigen-binding fragment" of an antibody refers to one or more fragments of an antibody that retain the ability to specifically bind to an antigen, such as CD40. It has been shown that the antigen-binding function of an antibody can be performed by fragments of a full-length antibody. Examples of binding fragments encompassed within the term "antigen-binding portion" of an antibody include a Fab fragment, a F(ab')$_2$ fragment, a Fab' fragment, a Fd fragment, a Fv fragment, a dAb fragment and an isolated complementarity determining region (CDR). Single chain antibodies such as scFv and heavy chain antibodies such as VHH and camel antibodies are also intended to be encompassed within the term "antigen-binding portion" of an antibody. These antibody fragments may be obtained using conventional techniques known to those of skill in the art, and the fragments may be screened for utility in the same manner as intact antibodies.

An antibody for use in the methods of the invention may be a human antibody. The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences—such antibodies are typically referred to as chimeric or humanised.

A human antibody for use the methods of the invention is typically a human monoclonal antibody. Such a human monoclonal antibody may be produced by a hybridoma which includes a B cell obtained from a transgenic nonhuman animal, e.g., a transgenic mouse, having a genome comprising a human heavy chain transgene and a light chain transgene fused to an immortalized cell. Human antibodies may also be prepared by in vitro immunisation of human lymphocytes followed by transformation of the lymphocytes with Epstein-Barr virus. The term "human antibody derivatives" refers to any modified form of the human antibody, e.g., a conjugate of the antibody and another agent or antibody.

An antibody for use in the methods of the invention may alternatively be a humanised antibody.

The term "humanised" refers to an antibody molecule, generally prepared using recombinant techniques, having an antigen binding site derived from an immunoglobulin from a non-human species and a remaining immunoglobulin structure based upon the structure and/or sequence of a human immunoglobulin. The antigen-binding site may comprise either complete non-human antibody variable domains fused to human constant domains, or only the complementarity determining regions (CDRs) of such variable domains grafted to appropriate human framework regions of human variable domains. The framework residues of such humanised molecules may be wild type (e.g., fully human) or they may be modified to contain one or more amino acid substitutions not found in the human antibody whose sequence has served as the basis for humanization.

Humanization lessens or eliminates the likelihood that a constant region of the molecule will act as an immunogen in human individuals, but the possibility of an immune response to the foreign variable region remains (LoBuglio, A. F. et al. (1989) "*Mouse/Human Chimeric Monoclonal Antibody In Man: Kinetics And Immune Response,*" Proc. Natl. Acad. Sci. (U.S.A.) 86:4220-4224). Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the antigens in question and determine binding capability, flanked by four framework regions (FRs) which are relatively conserved in a given species and which putatively provide a scaffolding for the CDRs. When nonhuman antibodies are prepared with respect to a particular antigen, the variable regions can be "reshaped" or "humanised" by grafting CDRs derived from nonhuman antibody on the FRs present in the human antibody to be modified. Application of this approach to various antibodies has been reported by Sato, K. et al. (1993) Cancer Res 53:851-856. Riechmann, L. et al. (1988) "*Reshaping Human Antibodies for Therapy,*" Nature 332:323-327; Verhoeyen, M. et al. (1988) "*Reshaping Human Antibodies: Grafting An Antilysozyme Activity,*" Science 239:1534-1536; Kettleborough, C. A. et al. (1991) "*Humanization Of A Mouse Monoclonal Antibody By CDR-Grafting: The Importance Of Framework Residues On Loop Conformation,*" Protein Engineering 4:773-3783; Maeda, H. et al. (1991) "*Construction Of Reshaped Human Antibodies With*

*HIV-Neutralizing Activity,"* Human Antibodies Hybridoma 2:124-134; Gorman, S. D. et al. (1991) *"Reshaping A Therapeutic CD4 Antibody,"* Proc. Natl. Acad. Sci. (U.S.A.) 88:4181-4185; Tempest, P. R. et al. (1991) *"Reshaping A Human Monoclonal Antibody To Inhibit Human Respiratory Syncytial Virus Infection in vivo,"* Bio/Technology 9:266-271; Co, M. S. et al. (1991) *"Humanized Antibodies For Antiviral Therapy,"* Proc. Natl. Acad. Sci. (U.S.A.) 88:2869-2873; Carter, P. et al. (1992) *"Humanization Of An Anti-p185her2 Antibody For Human Cancer Therapy,"* Proc. Natl. Acad. Sci. (U.S.A.) 89:4285-4289; and Co, M. S. et al. (1992) *"Chimeric And Humanized Antibodies With Specificity For The CD33 Antigen,"* J. Immunol. 148:1149-1154. In some embodiments, humanised antibodies preserve all CDR sequences (for example, a humanized mouse antibody which contains all six CDRs from the mouse antibodies). In other embodiments, humanised antibodies have one or more CDRs (one, two, three, four, five, six) which are altered with respect to the original antibody, which are also termed one or more CDRs "derived from" one or more CDRs from the original antibody. The ability to humanise an antigen is well known (see, e.g., U.S. Pat. Nos. 5,225,539; 5,530,101; 5,585,089; 5,859,205; 6,407,213; 6,881,557).

Any antibody referred to herein may be provided in isolated form or may optionally be provided linked (directly or indirectly) to another moiety. The other moiety may be a therapeutic molecule such as a cytotoxic moiety or a drug.

The therapeutic molecule may be directly attached, for example by chemical conjugation, to an antibody of the invention. Methods for conjugating molecules to an antibody are known in the art. For example, carbodiimide conjugation (Bauminger & Wilchek (1980) Methods Enzymol. 70, 151-159) may be used to conjugate a variety of agents, including doxorubicin, to antibodies or peptides. The water-soluble carbodiimide, 1-ethyl-3-(3-dimethylaminopropyl) carbodiimide (EDC) is particularly useful for conjugating a functional moiety to a binding moiety.

Other methods for conjugating a moiety to antibodies can also be used. For example, sodium periodate oxidation followed by reductive alkylation of appropriate reactants can be used, as can glutaraldehyde cross-linking. However, it is recognised that, regardless of which method of producing a conjugate of the invention is selected, a determination must be made that the antibody maintains its targeting ability and that the functional moiety maintains its relevant function.

A cytotoxic moiety may be directly and/or indirectly cytotoxic. By "directly cytotoxic" it is meant that the moiety is one which on its own is cytotoxic. By "indirectly cytotoxic" it is meant that the moiety is one which, although is not itself cytotoxic, can induce cytotoxicity, for example by its action on a further molecule or by further action on it. The cytotoxic moiety may be cytotoxic only when intracellular and is preferably not cytotoxic when extracellular.

Preferably, the antibody or antigen-binding fragment is linked to a cytotoxic moiety which is a directly cytotoxic chemotherapeutic agent. Optionally, the cytotoxic moiety is a directly cytotoxic polypeptide. Cytotoxic chemotherapeutic agents are well known in the art.

Cytotoxic chemotherapeutic agents, such as anticancer agents, include: alkylating agents including nitrogen mustards such as mechlorethamine (HN2), cyclophosphamide, ifosfamide, melphalan (L-sarcolysin) and chlorambucil; ethylenimines and methylmelamines such as hexamethylmelamine, thiotepa; alkyl sulphonates such as busulfane; nitrosoureas such as carmustine (BCNU), lomustine (CCNU), semustine (methyl-CCNU) and streptozocin (streptozotocin); and triazenes such as decarbazine (DTIC; dimethyltriazenoimidazole-carboxamide); Antimetabolites including folic acid analogues such as methotrexate (amethopterin); pyrimidine analogues such as fluorouracil (5-fluorouracil; 5-FU), floxuridine (fluorodeoxyuridine; FUdR) and cytarabine (cytosine arabinoside); and purine analogues and related inhibitors such as mercaptopurine (6-mercaptopurine; 6-MP), thioguanine (6-thioguanine; TG) and pentostatin (2'-deoxycoformycin). Natural Products including vinca alkaloids such as vinblastine (VLB) and vincristine; epipodophyllotoxins such as etoposide and teniposide; antibiotics such as dactinomycin (actinomycin D), daunorubicin (daunomycin; rubidomycin), doxorubicin, bleomycin, plicamycin (mithramycin) and mitomycin (mitomycin C); enzymes such as L-asparaginase; and biological response modifiers such as interferon alphenomes. Miscellaneous agents including platinum coordination complexes such as cisplatin (cis-DDP) and carboplatin; anthracenedione such as mitoxantrone and anthracycline; substituted urea such as hydroxyurea; methyl hydrazine derivative such as procarbazine (N-methylhydrazine, MIH); and adrenocortical suppressant such as mitotane (o,p'-DDD) and aminoglutethimide; taxol and analogues/derivatives; and hormone agonists/antagonists such as flutamide and tamoxifen.

The cytotoxic moiety may be a cytotoxic peptide or polypeptide moiety which leads to cell death. Cytotoxic peptide and polypeptide moieties are well known in the art and include, for example, ricin, abrin, *Pseudomonas* exotoxin, tissue factor and the like. Methods for linking them to targeting moieties such as antibodies are also known in the art. Other ribosome inactivating proteins are described as cytotoxic agents in WO 96/06641. *Pseudomonas* exotoxin may also be used as the cytotoxic polypeptide. Certain cytokines, such as TNFα and IL-2, may also be useful as cytotoxic agents.

Certain radioactive atoms may also be cytotoxic if delivered in sufficient doses. Thus, the cytotoxic moiety may comprise a radioactive atom which, in use, delivers a sufficient quantity of radioactivity to the target site so as to be cytotoxic. Suitable radioactive atoms include phosphorus-32, iodine-125, iodine-131, indium-111, rhenium-186, rhenium-188 or yttrium-90, or any other isotope which emits enough energy to destroy neighbouring cells, organelles or nucleic acid. Preferably, the isotopes and density of radioactive atoms in the agents of the invention are such that a dose of more than 4000 cGy (preferably at least 6000, 8000 or 10000 cGy) is delivered to the target site and, preferably, to the cells at the target site and their organelles, particularly the nucleus.

The radioactive atom may be attached to the antibody, antigen-binding fragment, variant, fusion or derivative thereof in known ways. For example, EDTA or another chelating agent may be attached to the binding moiety and used to attach 111In or 90Y. Tyrosine residues may be directly labelled with 125I or 131I.

The cytotoxic moiety may be a suitable indirectly-cytotoxic polypeptide. The indirectly cytotoxic polypeptide may be a polypeptide which has enzymatic activity and can convert a non-toxic and/or relatively non-toxic prodrug into a cytotoxic drug. With antibodies, this type of system is often referred to as ADEPT (Antibody-Directed Enzyme Prodrug Therapy). The system requires that the antibody locates the enzymatic portion to the desired site in the body of the patient and after allowing time for the enzyme to localise at the site, administering a prodrug which is a substrate for the enzyme, the end product of the catalysis being a cytotoxic compound. The object of the approach is to maximise the concentration of drug at the desired site and to minimise the concentration of drug in normal tissues. The cytotoxic moiety may be capable of converting a non-cytotoxic prodrug into a cytotoxic drug.

The enzyme and prodrug of the system using a targeted enzyme as described herein may be any of those previously proposed. The cytotoxic substance may be any existing anti-cancer drug such as an alkylating agent; an agent which intercalates in DNA; an agent which inhibits any key enzymes such as dihydrofolate reductase, thymidine synthetase, ribonucleotide reductase, nucleoside kinases or topoisomerase; or an agent which effects cell death by interacting with any other cellular constituent. Etoposide is an example of a topoisomerase inhibitor.

Reported prodrug systems include those listed in Table 1.

TABLE 1

| Enzyme | Prodrug |
| --- | --- |
| Carboxypeptidase G2 | Derivatives of L-glutamic acid and benzoic acid mustards, aniline mustards, phenol mustards and phenylenediamine mustards; fluorinated derivatives of these |
| Alkaline phosphatase | Etoposide phosphate<br>Mitomycin phosphate |
| Beta-glucuronidase | p-Hydroxyaniline mustard-glucuronide<br>Epirubicin-glucuronide |
| Penicillin-V-amidase | Adriamycin-N phenoxyacetyl |
| Penicillin-G-amidase | N-(4'-hydroxyphenyl acetyl) palytoxin<br>Doxorubicin and melphalan |
| Beta-lactamase | Nitrogen mustard-cephalosporin p-phenylenediamine; doxorubicin derivatives; vinblastine derivative-cephalosporin, cephalosporin mustard; a taxol derivative |
| Beta-glucosidase | Cyanophenylmethyl-beta-D-gluco-pyranosiduronic acid |
| Nitroreductase | 5-(Azaridin-1-yl-)-2,4-dinitrobenzamide |
| Cytosine deaminase | 5-Fluorocytosine |
| Carboxypeptidase A | Methotrexate-alanine |

Suitable enzymes for forming part of an enzymatic portion include: exopeptidases, such as carboxypeptidases G, G1 and G2 (for glutamylated mustard prodrugs), carboxypeptidases A and B (for MTX-based prodrugs) and aminopeptidases (for 2-α-aminocyl MTC prodrugs); endopeptidases, such as e.g. thrombolysin (for thrombin prodrugs); hydrolases, such as phosphatases (e.g. alkaline phosphatase) or sulphatases (e.g. aryl sulphatases) (for phosphylated or sulphated prodrugs); amidases, such as penicillin amidases and arylacyl amidase; lactamases, such as β-lactamases; glycosidases, such as β-glucuronidase (for β-glucuronomide anthracyclines), α-galactosidase (for amygdalin) and β-galactosidase (for β-galactose anthracycline); deaminases, such as cytosine deaminase (for 5FC); kinases, such as urokinase and thymidine kinase (for gancyclovir); reductases, such as nitroreductase (for CB1954 and analogues), azoreductase (for azobenzene mustards) and DT-diaphorase (for CB1954); oxidases, such as glucose oxidase (for glucose), xanthine oxidase (for xanthine) and lactoperoxidase; DL-racemases, catalytic antibodies and cyclodextrins.

Preferably, the prodrug is relatively non-toxic compared to the cytotoxic drug. Typically, it has less than 10% of the toxicity, preferably less than 1% of the toxicity as measured in a suitable in vitro cytotoxicity test.

It is likely that the moiety which is able to convert a prodrug to a cytotoxic drug will be active in isolation from the rest of the agent of the invention but it is necessary only for it to be active when (a) it is in combination with the rest of the agent of the invention and (b) the agent of the invention is attached to, adjacent to or internalised in target cells.

When each moiety is a polypeptide, the two portions may be linked together by any of the conventional ways of cross-linking polypeptides. For example, the antibody or antigen-binding fragment may be enriched with thiol groups and the further moiety reacted with a bifunctional agent capable of reacting with those thiol groups, for example the N-hydroxysuccinimide ester of iodoacetic acid (NHIA) or N-succinimidyl-3-(2-pyridyldithio)propionate (SPDP). Amide and thioether bonds, for example achieved with m-maleimidobenzoyl-N-hydroxysuccinimide ester, are generally more stable in vivo than disulphide bonds.

The cytotoxic moiety may be a radiosensitizer. Radiosensitizers include fluoropyrimidines, thymidine analogues, hydroxyurea, gemcitabine, fludarabine, nicotinamide, halogenated pyrimidines, 3-aminobenzamide, 3-aminobenzodiamide, etanixadole, pimonidazole and misonidazole. Also, delivery of genes into cells can radiosensitise them, for example delivery of the p53 gene or cyclin D. The further moiety may be one which becomes cytotoxic, or releases a cytotoxic moiety, upon irradiation. For example, the boron-10 isotope, when appropriately irradiated, releases a particles which are cytotoxic. Similarly, the cytotoxic moiety may be one which is useful in photodynamic therapy such as photofrin.

Antibodies Specific for CD40

The combination therapies and methods of the invention utilise an antibody that binds immunospecifically to CD40, that is an "anti-CD40 antibody". In one embodiment, said antibody is retained at the tumour site following administration to a subject (see discussion under step (a) above)). The antibody preferably specifically binds to CD40, that is it binds to CD40 but does not bind, or binds at a lower affinity (e.g. a 10-fold lower affinity), to other molecules. Unless otherwise specified, the term CD40 as used herein refers to human CD40. The sequence of human CD40 is set out in SEQ ID NO: 13. An anti-CD40 antibody of the present invention may have some binding affinity for CD40 from other mammals, for example primate or murine CD40. The antibody preferably binds to human CD40 when localised on the surface of a cell.

In particular, the anti-CD40 antibodies used in the combination therapies of the invention compete for binding to human CD40 with a 'reference antibody' which comprises the light chain variable region of SEQ ID NO: 7 and the heavy chain variable region of SEQ ID NO: 8 (optionally together with light and heavy constant regions of SEQ ID NO:11 and SEQ ID NO:12, respectively). Such competitive binding inhibition can be determined using assays and methods well known in the art, for example using BIAcore chips with immobilised human CD40 and incubating in the presence of the reference antibody, with and without an antibody polypeptide to be tested. Alternatively, a pair-wise mapping approach can be used, in which the reference antibody is immobilised to the surface of the BIAcore chip, human CD40 is bound to the immobilised antibody, and then a second antibody is tested for simultaneous binding ability to human CD40 (see 'BIAcore Assay Handbook', GE Healthcare Life Sciences, 29-0194-00 AA May 2012; the disclosures of which are incorporated herein by reference).

Exemplary anti-CD40 antibodies are disclosed in WO 2013/034904 to Alligator Bioscience AB (the disclosures of which are incorporated herein by reference).

The antibody preferably has the ability to bind to CD40 in its native state and in particular to CD40 localised on the surface of a cell. Preferably, an antibody will bind specifically to CD40. That is, an antibody used in the methods of invention will preferably bind to CD40 with greater binding affinity than that at which it binds to another molecule.

By "localised on the surface of a cell" it is meant that CD40 is associated with the cell such that one or more region of CD40 is present on the outer face of the cell surface. For example, CD40 may be inserted into the cell plasma membrane (i.e. orientated as a transmembrane protein) with one or more regions presented on the extracellular surface. This may occur in the course of expression of CD40 by the cell. Thus, in one embodiment, "localised on the surface of a cell" may mean "expressed on the surface of a cell." Alternatively, CD40 may be outside the cell with covalent and/or ionic interactions localising it to a specific region or regions of the cell surface.

An anti-CD40 antibody used in the combination therapies and methods of the invention may induce and/or enhance ADCC-mediated lysis of a cell expressing CD40 and/or enhance apoptosis of a cell expressing CD40. The cell is typically a tumour cell. By "enhance" it is meant that the number of cells lysed or apoptosed increases in the presence of an antibody of the invention, relative to the number of cells lysed or apoptosed in the presence of an appropriate control substance. Methods for determining the level of ADCC-mediated lysis or apoptosis in a sample of cells are well known in the art. For example, a chromium-51 release assay, europium release assay or sulphur-35 release assay may be used. In such assays, a previously labelled target cell line expressing the antigen (in this case CD40) is incubated with an antibody to be tested. After washing, effector cells (typically expressing Fc receptor CD16) are co-incubated with the antibody-labelled target cells. Target cell lysis is subsequently measured by release of intracellular label by a scintillation counter or spectrophotometry.

Preferably, the antibody, antigen-binding fragment, comprises an antibody Fc-region. It will be appreciated by skilled person that the Fc portion may be from an IgG antibody, or from a different class of antibody (such as IgM, IgA, IgD or IgE). For example, the Fc region may be from an IgG1, IgG2, IgG3 or IgG4 antibody. Advantageously, however, the Fc region is from an IgG1 antibody.

The Fc region may be naturally-occurring (e.g. part of an endogenously produced antibody) or may be artificial (e.g. comprising one or more point mutations relative to a naturally-occurring Fc region). Fc-regions with point mutations improving their ability to bind FcR may be advantageous, e.g. by altering serum half life or improve binding to Fcγ receptors (FcγR) involved in ADCC and CDC. In particular, mutations that enhance binding to FcγRIIB, e.g. S267E (Strohl et al., 2009, Curr Opin Biotechnol, 20:685-691) may be advantageous for the invention giving the link between FcγRIIB binding and functional activity of CD40 antibodies (Li et al., 2011, Science, 333: 1030-1034).

As an alternative to the labelling with radioisotopes required in such assays, methods may be used in which lysis is detected by measuring the release of enzymes naturally present in the target cells. This may be achieved by detection (for example bioluminescent detection) of the products of an enzyme-catalysed reaction. No previous labelling of the cells is required in such an assay. A typical cellular enzyme detected with such an assay is GAPDH.

An anti-CD40 antibody used in the combination therapies and methods of the invention may modulate the activity of a cell expressing CD40, wherein said modulation is an increase or decrease in the activity of said cell. The cell is typically a dendritic cell or a B cell.

Professional APCs, such as dendritic cells, are activated when signaling via CD40 occurs, which triggers several biological events, including immune cell activation, proliferation, and production of cytokines and chemokines. Methods for determining dendritic cell activation associated with CD40 are known in the art (discussed, for example, in Schonbeck et al., 2001, Cell Mol Life Sci., 58:40-43; van Kooten et al., 2000, J. Leuk., Biol., 67: 2-17) and are described further below.

Stimulation of human B cells with recombinant CD40L or anti-CD40 antibodies induces up-regulation of surface markers, such as CD23, CD30, CD80, CD86, Fas and MHC II, secretion of soluble cytokines, e.g. IL-6, TNF-γ and TNF-α, and homeotypic aggregation. Methods for determining CD40-related B cell activation are known in the art (discussed, for example, in Schonbeck et al., 2001, supra) and are described further below.

Methods and assays for determining the ability of an antibody to modulate the activity of dendritic cells and B cells are well known in the art. For example, the activation of dendritic cells may be assessed by measuring the level of cell surface markers such as CD86 and CD80 and/or by measuring anti-CD40 antibody-induced secretion of IFNγ from T cells, wherein in an increase in any of these parameters indicates increased activation and a decrease represents decreased activation. Similarly, the ability of an antibody to modulate the activity of B cells may be assessed by measuring the level of cell surface markers (such as CD86) and/or by measuring anti-CD40 antibody-induced B cell proliferation (see Example 3 below), wherein in an increase in any of these parameters indicates increased activation and a decrease represents decreased activation.

Preferably, an anti-CD40 antibody used in the combination therapies and methods of the invention which increases the activation of dendritic cells or B cells has a potency for dendritic cell or B cell activation. Cell activation may typically be measured as an EC50 level in an assay which involves incubating isolated dendritic or B cells with the test stimulator and then detecting cell proliferation as the measure of activation.

The terms "binding activity" and "binding affinity" are intended to refer to the tendency of an antibody molecule to bind or not to bind to a target. Binding affinity may be quantified by determining the dissociation constant (Kd) for an antibody and its target. Similarly, the specificity of binding of an antibody to its target may be defined in terms of the comparative dissociation constants (Kd) of the antibody for its target as compared to the dissociation constant with respect to the antibody and another, non-target molecule.

Typically, the Kd for the antibody with respect to the target will be 2-fold, preferably 5-fold, more preferably 10-fold less than Kd with respect to the other, non-target molecule such as unrelated material or accompanying material in the environment. More preferably, the Kd will be 50-fold less, even more preferably 100-fold less, and yet more preferably 200-fold less.

The value of this dissociation constant can be determined directly by well-known methods, and can be computed even for complex mixtures by methods such as those, for example, set forth in Caceci et al. (Byte 9:340-362, 1984). For example, the Kd may be established using a double-filter nitrocellulose filter binding assay such as that disclosed by Wong & Lohman (Proc. Natl. Acad. Sci. USA 90, 5428-5432, 1993). Other standard assays to evaluate the binding ability of ligands such as antibodies towards targets are known in the art, including for example, ELISAs, Western blots, RIAs, and flow cytometry analysis. The binding kinetics (e.g., binding affinity) of the antibody also can be assessed by standard assays known in the art, such as by Biacore™ system analysis.

A competitive binding assay can be conducted in which the binding of the antibody to the target is compared to the binding of the target by another, known ligand of that target, such as another antibody. The concentration at which 50% inhibition occurs is known as the Ki. Under ideal conditions, the Ki is equivalent to Kd. The Ki value will never be less than the Kd, so measurement of Ki can conveniently be substituted to provide an upper limit for Kd.

An anti-CD40 antibody used in the combination therapies and methods of the invention is preferably capable of binding to its target with an affinity that is at least two-fold, 10-fold, 50-fold, 100-fold or greater than its affinity for binding to another non-target molecule.

An antibody used in the combination therapies and methods of the invention will typically exhibit the ability to:
(i) specifically bind to human CD40 when localised on the surface of a cell; and/or
(ii) enhance antibody dependent cellular cytotoxicity (ADCC)-mediated lysis of a cell expressing CD40; and/or
(iii) enhance apoptosis of a cell expressing CD40; and/or
(iv) modulate the activity of a cell expressing CD40, wherein said modulation is an increase or decrease in the activity of said cell.

The antibody may be or may comprise a variant or a fragment of one of the specific anti-CD40 antibodies disclosed herein, provided that said variant or fragment retains specificity for CD40, and at least one of functional characteristics (i) to (iv).

A fragment is preferably an antigen binding portion of a said antibody. A fragment may be made by truncation, e.g. by removal of one or more amino acids from the N and/or C-terminal ends of a polypeptide. Up to 10, up to 20, up to 30, up to 40 or more amino acids may be removed from the N and/or C terminal in this way. Fragments may also be generated by one or more internal deletions.

A variant may comprise one or more substitutions, deletions or additions with respect to the sequences of a specific antib-CD40 antibody disclosed herein. A variant may comprise 1, 2, 3, 4, 5, up to 10, up to 20, up to 30 or more amino acid substitutions and/or deletions from the specific sequences disclosed herein. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid.

Some properties of the 20 main amino acids which can be used to select suitable substituents are as follows:

| Ala | aliphatic, hydrophobic, neutral | Met | hydrophobic, neutral |
|---|---|---|---|
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

Preferred "variants" include those in which instead of the naturally occurring amino acid the amino acid which appears in the sequence is a structural analog thereof. Amino acids used in the sequences may also be derivatized or modified, e.g. labelled, providing the function of the antibody is not significantly adversely affected.

Variants may be prepared during synthesis of the antibody or by post-production modification, or when the antibody is in recombinant form using the known techniques of site-directed mutagenesis, random mutagenesis, or enzymatic cleavage and/or ligation of nucleic acids.

Preferably variant antibodies have an amino acid sequence which has more than 60%, or more than 70%, e.g. 75 or 80%, preferably more than 85%, e.g. more than 90 or 95% amino acid identity to the VL or VH domain of an antibody disclosed herein. This level of amino acid identity may be seen across the full length of the relevant SEQ ID NO sequence or over a part of the sequence, such as across 20, 30, 50, 75, 100, 150, 200 or more amino acids, depending on the size of the full length polypeptide.

In connection with amino acid sequences, "sequence identity" refers to sequences which have the stated value when assessed using ClustalW (Thompson et al., 1994, supra) with the following parameters:

Pairwise alignment parameters -Method: accurate, Matrix: PAM, Gap open penalty: 10.00, Gap extension penalty: 0.10;

Multiple alignment parameters-Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: GPSNDQEKR. Sequence identity at a particular residue is intended to include identical residues which have simply been derivatized.

An anti-CD40 antibody for use in the combination therapies and methods of the invention may bind to the same epitope as a specific antibody as disclosed herein, since such an antibody is likely to mimic the action of the disclosed antibody. Whether or not an antibody binds to the same epitope as another antibody may be determined by routine methods. For example, the binding of each antibody to a target may be using a competitive binding assay. Methods for carrying out competitive binding assays are well known in the art. For example they may involve contacting together an antibody and a target molecule under conditions under which the antibody can bind to the target molecule. The antibody/target complex may then be contacted with a second (test) antibody and the extent to which the test antibody is able to displace the first antibody from antibody/target complexes may be assessed. Such assessment may use any suitable technique, including, for example, Surface Plasmon Resonance, ELISA, or flow cytometry. The ability of a test antibody to inhibit the binding of a first antibody to the target demonstrates that the test antibody can compete with said first antibody for binding to the target and thus that the test antibody binds to the same epitope or region on the target as the first antibody, and may therefore mimic the action of the first antibody.

An anti-CD40 antibody used in the combination therapies and methods of the invention may be an antibody comprising one, two or all three of the CDR sequences of SEQ ID NOs: 1 to 3 and/or one, two, or all three of the CDR sequences of SEQ ID NOs: 4 to 6. The antibody may comprise all six CDR sequences of SEQ ID NOs: 1 to 6.

The antibody may comprise the light chain variable region sequence of SEQ ID NO: 7 and/or the heavy chain variable region sequence of SEQ ID NO: 8.

The antibody may be, or may bind to the same epitope as, an antibody comprising the light chain variable region sequence of SEQ ID NO: 7 and the heavy chain variable region sequence of SEQ ID NO: 8. In addition, the antibody may comprise the light chain constant region sequence of SEQ ID NO: 11 and/or the heavy chain constant region sequence of SEQ ID NO: 12.

The anti-CD40 antibody or any variant or fragment thereof used in the combination therapies and methods of the invention preferably has a theoretical isoelectric point (pI) of 9.0 or above, preferably 9.1 or above, more preferably 9.2 or above or 9.25 or above, most preferably 9.3 or above.

Combination Therapies

The invention provides a combination therapy for use in treating a solid tumour in a subject comprising (a) an antibody, or antigen-binding portion thereof, that specifically binds to CD40, and (b) a further immunotherapeutic agent with efficacy in the treatment of cancer, which agent is not an anti-CD40 antibody or antigen-binding fragment thereof, wherein the antibody or antigen-binding portion thereof that specifically binds to CD40 competes for binding to human CD40 with an antibody which comprises the light chain variable region of SEQ ID NO: 7 and the heavy chain variable region of SEQ ID NO: 8 and wherein the further immunotherapeutic agent specifically binds to an immune checkpoint molecule.

The terms "combination therapy" or "combined treatment" or "in combination" as used herein denotes any form of concurrent or parallel treatment with at least two distinct therapeutic agents.

According to certain embodiments, the anti-CD40 antibody, or antigen-binding fragment thereof, and the immunotherapeutic agent that specifically binds to an immune checkpoint molecule other than CD40 are administered simultaneously, either in the same composition or in separate compositions. According to other embodiments, the anti-CD40 antibody, or antigen-binding fragment thereof, and the immunotherapeutic agent that specifically binds to an immune checkpoint molecule other than CD40 are administered sequentially, i.e., the anti-CD40 antibody, or antigen-binding fragment thereof, is administered either prior to or after the administration of the immunotherapeutic agent that specifically binds to an immune checkpoint molecule other than CD40. In some embodiments, the administration of the anti-CD40 antibody, or antigen-binding fragment thereof, and the immunotherapeutic agent that specifically binds to an immune checkpoint molecule other than CD40 are concurrent, i.e., the administration period of the anti-CD40 antibody, or antigen-binding fragment thereof, and that of the immunotherapeutic agent that specifically binds to an immune checkpoint molecule other than CD40 overlap with each other. In some embodiments, the administration of the anti-CD40 antibody, or antigen-binding fragment thereof, and the immunotherapeutic agent that specifically binds to an immune checkpoint molecule other than CD40 are non-concurrent. For example, in some embodiments, the administration of the anti-CD40 antibody, or antigen-binding fragment thereof, is terminated before the immunotherapeutic agent that specifically binds to an immune checkpoint molecule other than CD40 is administered. In some embodiments, the administration of immunotherapeutic agent that specifically binds to an immune checkpoint molecule other than CD40 is terminated before the anti-CD40 antibody, or antigen-binding fragment thereof, is administered.

According to certain typical embodiments, the anti-CD40 antibody, or antigen-binding fragment thereof, and the immunotherapeutic agent that specifically binds to an immune checkpoint molecule other than CD40 are administered within a single therapeutic composition. According to some embodiments, the therapeutic composition further comprises therapeutically acceptable diluents or carrier.

The further component of the combinations therapies of the invention is an immunotherapeutic agent with efficacy in the treatment of cancer, which agent is not an anti-CD40 antibody or antigen-binding fragment thereof.

The term "immunotherapeutic agent" is intended to include any molecule, peptide, antibody or other agent which can stimulate a host immune system to generate an immune response to a tumour or cancer in the subject. Various immunotherapeutic agents are useful in the compositions and methods described herein. In one embodiment, the immunotherapeutic agent is an antibody or antigen-binding fragment thereof.

The term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages.

The term "immune checkpoint molecule" is intended to include a group of proteins on the cell surface of immune cells, such as CD4+ and/or CD8+ T cells, dendritic cells, NK cells and macrophages but also on certain tumor cells, that modulate immune responses. It will be appreciated by persons skilled in the art that an immune check point proteins may be either inhibitory, e.g. CTLA-4 and PD-1, or stimulatory, e.g. OX40 and CD137. Exemplary immune checkpoint molecule include, without limitation, PD-1, CTLA-4, OX40 (CD134), CD137, VISTA, B7-H2, B7-H3, PD-L 1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, and A2aR. In a preferred embodiment, the immune checkpoint molecule is PD-1, CTLA-4, OX40 (CD134) or CD137.

Blocking or neutralisation of one or more inhibitory immune checkpoint molecules can block or otherwise neutralise inhibitory signalling to thereby upregulate an immune response in order to more efficaciously treat cancer. Exemplary agents useful for blocking inhibitory immune checkpoint include antibodies, small molecules, peptides, peptidomimetics, natural ligands, and derivatives of natural ligands, that can either bind and/or inactivate or inhibit inhibitory immune checkpoint proteins, or fragments thereof; as well as RNA interference, antisense, nucleic acid aptamers, etc. that can downregulate the expression and/or activity of inhibitory immune checkpoint nucleic acids, or fragments thereof. Exemplary agents for upregulating an immune response include antibodies against one or more inhibitory immune checkpoint proteins that blocks the interaction between the proteins and its natural receptor(s); a non-activating form of one or more immune checkpoint inhibitor proteins {e.g., a dominant negative polypeptide): small molecules or peptides that block the interaction between one or more inhibitory immune checkpoint proteins and its natural receptor(s); fusion proteins (e.g. the extracellular portion of an immune checkpoint inhibition protein fused to the Fc portion of an antibody or immunoglobulin) that bind to its natural receptor(s); nucleic acid molecules that block inhibitory immune checkpoint nucleic acid transcription or translation; and the like. Such agents can directly block the interaction between the one or more inhibitory immune checkpoint and its natural receptor(s) (e.g., antibodies) to prevent inhibitory signalling and upregulate an immune response. Alternatively, agents can indirectly block the interaction between one or more inhibitory immune checkpoint proteins and its natural receptor(s) to prevent inhibitory signalling and upregulate an immune response. For example, a soluble version of an immune checkpoint protein ligand such as a stabilized extracellular domain can binding to its receptor to indirectly reduce the effective concentration of the receptor to bind to an appropriate ligand. In one embodiment, anti-PD-1 antibodies, anti-PD-L1 antibodies, and anti-CTLA-4 antibodies, either alone or in combination, are used to inhibit immune checkpoint inhibitors.

Thus, in one embodiment, the immunotherapeutic agent that specifically binds to an immune checkpoint molecule other than CD40 is an antibody, or antigen-binding fragment thereof, that binds to and inhibits the function of an inhibitory immune checkpoint molecule.

Activation of one or more stimulatory immune checkpoint molecules can upregulate an immune response in order to more efficaciously treat cancer. Exemplary agents useful for activating stimulatory immune checkpoint include antibodies, small molecules, peptides, peptidomimetics, natural ligands, and derivatives of natural ligands, that can activate stimulatory immune checkpoint proteins, or fragments thereof; as well as RNA interference, antisense, nucleic acid aptamers, etc. that can enhance the immune checkpoint nucleic acids, or fragments thereof. Exemplary agents for upregulating an immune response include a soluble version of a stimulatory immune checkpoint protein ligand, or such ligand fused to an Fc or a domain that facilitate a multimerization of the ligand. In one embodiment, anti-CD137 and anti-OX40 antibodies either alone or in combination, are used to activate stimulatory immune checkpoint inhibitors.

Thus, in an alternative embodiment, the immunotherapeutic agent that specifically binds to an immune checkpoint molecule other than CD40 is an antibody, or antigen-binding fragment thereof, that binds to and activates the function of a stimulatory immune checkpoint molecule.

Preferred examples of checkpoint molecules include PD1, which serves as a negative regulator of T cell activation when engaged with its ligands PD-L1 or PD-L2. PD-L1 in particular is expressed by many solid tumors, including melanoma. These tumours may therefore down regulate immune mediated anti-tumor effects through activation of the inhibitory PD-1 receptors on T cells. By blocking the interaction between PD1 and PD-L1, a check point of the immune response may be removed, leading to augmented anti-tumour T cell responses. This interaction may be blocked by an antibody specific for PD1 or PD-L1or any other suitable agent. Such antibodies and agents may be generally referred to as PD1 inhibitors. PD1 inhibitors are particularly preferred as the additional therapeutic agent in step (b) of the method of the invention.

Anti-PD1 antibodies include Nivolumab, Pembrolizumab, Lambrolizumab, Pidilzumab, and AMP-224. Anti-PD-L1 antibodies include MEDI-4736 and MPDL3280A.

The combination of a systemic PD1 inhibitor and a local anti-CD40 antibody is not just attractive because of the expression of PD-L1 by tumours. Such a combination could also be beneficial in modulating the general immunosuppressive environment, by affecting the regulatory T-cells and myeloid-derived suppressor cells (MSDCs). For example, CD40 agonists such as the anti-CD40 antibody used in the method of the invention will modulate the CD40 positive tumor associated M2 macrophages and MSDCs, whereas the PD1 inhibitor will modulate regulatory T-cells and MSDCs. Moreover, as explained above (see discussion regarding the timing of steps (a) and (b)), ligation of CD40 by antibodies has been reported to activate and mature dendritic cells that upon maturation will up-regulate PD-L 1 and 2 providing further rationale for combining the two treatments. Further, CD40 agonists such as the anti-CD40 antibody used in the method of the invention will indirectly upregulate PD-1 on T cells and PD-L1 on tumors and tumor infiltrating cells. Hence, treatment of solid tumour (such as melanoma) with a combination of a systemic PD1 inhibitor and an anti-CD40 antibody that is retained at the tumour site would have pleiotropic effects both by activating the immune system and by suppressing the counter-regulatory signals.

Another example of checkpoint molecule is the T cell receptor CTLA-4, which serves as a negative regulator of T cell activation. Ordinarily it is upregulated on the T-cell surface following initial activation. The ligands of the CTLA-4 receptor are the B7 proteins (B7-1 and B7-2), which are expressed by antigen presenting cells. The corresponding receptor responsible for the upregulation of T cell activation is CD28, which competes for binding to the B7 proteins with CTLA-4. Thus, by blocking the CTLA-4 interaction with the B7 proteins, but not the CD28 interaction with the B7 proteins, one of the normal check points of the immune response may be removed, leading to augmented anti-tumour T cell responses. Blocking the CTLA-4 interaction with the B7 proteins may be achieved with an anti-CTLA-4 antibody or other suitable agent. Anti-CTLA-4 antibodies include ipilumumab, tremelimumab, or any of the antibodies disclosed in PCT/EP2014/063442. Other molecules include polypeptides, or soluble mutant CD86 polypeptides.

Thus, the additional therapeutic agent may preferably be an antibody or other agent which specifically binds to at least one of PD1, PD-L1 or CTLA-4.

The additional therapeutic agent is most preferably a PD1 inhibitor, such as an anti-PD1 or anti-PD-L1 antibody, selected from Nivolumab, Pembrolizumab, Lamborlizumab, Pdilizumab, MEDT-4736, and MPDL3280A.

Where the additional therapeutic agent is an antibody or bi-specific molecule comprising an antibody, it will be understood that all of the general considerations set out above regarding the definitions of antibodies, antigen-binding fragments of antibodies, optional conjugation to additional therapeutic moieties etc, also apply to an antibody that is the additional therapeutic agent. Similarly, it will be understood that the definitions of target specificity/affinity and methods for determining specificity/affinity set out above for anti-CD40 antibodies will apply equally to an antibody that is the additional therapeutic agent, except the specific target of the agent will be read in place of CD40.

Variants and fragments of an antibody which is the additional therapeutic agent may also be defined in the same way as the variants and fragments of anti-CD40 antibodies.

Kits and Pharmaceutical Compositions

The invention also provides a kit for treating a solid tumour in a subject, the kit comprising a combination therapy as defined above. For example, the kit may comprise (a) a therapeutically effective amount of an antibody that specifically binds to CD40 and that is retained at the tumour site following administration and optionally (b) a therapeutically effective amount of an additional therapeutic agent that is suitable for systemic administration to a subject. The antibody that specifically binds to CD40 is preferably provided in a form suitable for local administration to a tumour site.

The kits of the invention may additionally comprise one or more other reagents or instruments which enable any of the embodiments mentioned above to be carried out. Such reagents or instruments include one or more of the following: suitable buffer(s) (aqueous solutions) and means to administer the anti-CD40 antibody and/or the additional therapeutic agent (such as a vessel or an instrument comprising a needle).

The anti-CD40 antibody and the additional therapeutic agent used in the methods of the invention, or provided in the kits of the invention, may each be provided as a separate pharmaceutical composition formulated together with a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible and are also compatible with the required routes of administration.

Thus, the carrier for the anti-CD40 antibody and the additional therapeutic agent may be suitable for systemic administration, which as defined above means administration into the circulatory system of the subject, including the vascular and/or lymphatic system. Such administration may be by any suitable route, but is typically parenteral. The phrase "parenteral administration" as used herein means modes of administration other than enteral and topical administration, and is typically achieved by injection, infusion or implantation. Suitable routes include intravenous, intramuscular, intradermal, intraperitoneal, subcutaneous, spinal or other parenteral routes of administration.

However, the carrier for the anti-CD40 antibody is preferably suitable for local administration, which as defined above includes peritumoral, juxtatumoral, intratumoral, intralesional, perilesional, intracranial and intravesicle administration by any suitable means, such as injection. Local administration may also include intra cavity infusion and inhalation, depending on the site of the tumour.

Depending on the route of administration, the antibody and/or the agent may be coated in a material to protect the antibody from the action of acids and other natural conditions that may inactivate or denature the antibody and/or agent. Preferred pharmaceutically acceptable carriers comprise aqueous carriers or diluents. Examples of suitable aqueous carriers that may be employed in the pharmaceutical compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. In many cases, it will be preferable to include isotonic agents, for example, sugars, polyalcohols such as mannitol, sorbitol, or sodium chloride in the composition.

It will be appreciated by persons skilled in the art that the antibody components of the combination therapies of the present invention are typically provided in the form of one or more pharmaceutical compositions, each containing a therapeutically-effective amount of the antibody component(s) together with a pharmaceutically-acceptable buffer, excipient, diluent or carrier.

A 'therapeutically effective amount', or 'effective amount', or 'therapeutically effective', as used herein, refers to that amount which provides a therapeutic effect for a given condition and administration regimen. This is a predetermined quantity of active antibody calculated to produce a desired therapeutic effect in association with the required additive and diluent, i.e. a carrier or administration vehicle. Further, it is intended to mean an amount sufficient to reduce or prevent a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent.

A therapeutically effective amount can be determined by the ordinary skilled medical or veterinary worker based on patient characteristics, such as age, weight, sex, condition, complications, other diseases, etc., as is well known in the art.

A pharmaceutical composition may include a pharmaceutically acceptable anti-oxidant. These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutical compositions typically must be sterile and stable under the conditions of manufacture and storage. The composition can be formulated as a solution, microemulsion, liposome, or other ordered structure suitable to high drug concentration. Sterile injectable solutions can be prepared by incorporating the active agent (e.g. antibody) in the required amount in an appropriate solvent with one or a combination of ingredients enumerated above, as required, followed by sterilization microfiltration. Generally, dispersions are prepared by incorporating the active agent into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active agent plus any additional desired ingredient from a previously sterile-filtered solution thereof. Pharmaceutical compositions may comprise additional active ingredients as well as those mentioned above.

Suitable pharmaceutically acceptable buffers, diluents, carriers and excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed ., Pharmaceutical Press (2000), the disclosures of which are incorporated herein by reference).

The term "buffer" is intended to include an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

The term "diluent" is intended to include an aqueous or non-aqueous solution with the purpose of diluting the agent in the pharmaceutical preparation. The diluent may be one or more of saline, water, polyethylene glycol, propylene glycol, ethanol or oils (such as safflower oil, corn oil, peanut oil, cottonseed oil or sesame oil).

The term "adjuvant" is intended to include any compound added to the formulation to increase the biological effect of the agent of the invention. The adjuvant may be one or more of zinc, copper or silver salts with different anions, for example, but not limited to fluoride, chloride, bromide, iodide, tiocyanate, sulfite, hydroxide, phosphate, carbonate, lactate, glycolate, citrate, borate, tartrate, and acetates of different acyl composition. The adjuvant may also be cationic polymers such as cationic cellulose ethers, cationic cellulose esters, deacetylated hyaluronic acid, chitosan, cationic dendrimers, cationic synthetic polymers such as poly (vinyl imidazole), and cationic polypeptides such as polyhistidine, polylysine, polyarginine, and peptides containing these amino acids.

The excipient may be one or more of carbohydrates, polymers, lipids and minerals. Examples of carbohydrates include lactose, glucose, sucrose, mannitol, and cyclodextrines, which are added to the composition, e.g., for facilitating lyophilisation. Examples of polymers are starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone, all of different molecular weight, which are added to the composition, e.g., for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The active antibody-based agents of the invention may be formulated into any type of pharmaceutical composition known in the art to be suitable for the delivery thereof.

In one embodiment, the pharmaceutical compositions of the invention may be in the form of a liposome, in which the agent is combined, in addition to other pharmaceutically acceptable carriers, with amphipathic agents such as lipids, which exist in aggregated forms as micelles, insoluble monolayers and liquid crystals. Suitable lipids for liposomal formulation include, without limitation, monoglycerides, diglycerides, sulfatides, lysolecithin, phospholipids, saponin, bile acids, and the like. Suitable lipids also include the lipids above modified by poly(ethylene glycol) in the polar headgroup for prolonging bloodstream circulation time. Preparation of such liposomal formulations is can be found in for example U.S. Pat. No. 4,235,871, the disclosures of which are incorporated herein by reference.

The pharmaceutical compositions of the invention may also be in the form of biodegradable microspheres. Aliphatic polyesters, such as poly(lactic acid) (PLA), poly(glycolic acid) (PGA), copolymers of PLA and PGA (PLGA) or poly(carprolactone) (PCL), and polyanhydrides have been widely used as biodegradable polymers in the production of microspheres. Preparations of such microspheres can be found in U.S. Pat. No. 5,851,451 and in EP 0 213 303, the disclosures of which are incorporated herein by reference.

In a further embodiment, the pharmaceutical compositions of the invention are provided in the form of nanoparticles, for example based on poly-gamma glutamic acid. Details of the preparation and use of such nanoparticles can be found in WO 2011/128642, the disclosures of which are incorporated herein by reference. It will be appreciated by persons skilled in the art that one or more of the active components of the combination therapies of the present invention may be formulated in separate nanoparticles, or both active components may be formulated in the same nanoparticles.

In a further embodiment, the pharmaceutical compositions of the invention are provided in the form of polymer gels, where polymers such as starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polyvinyl imidazole, polysulphonate, polyethylenglycol/polyethylene oxide, polyethyleneoxide/polypropylene oxide copolymers, polyvinylalcohol/ polyvinylacetate of different degree of hydrolysis, and polyvinylpyrrolidone are used for thickening of the solution containing the agent. The polymers may also comprise gelatin or collagen.

Alternatively, the agents may simply be dissolved in saline, water, polyethylene glycol, propylene glycol, ethanol or oils (such as safflower oil, corn oil, peanut oil, cottonseed oil or sesame oil), tragacanth gum, and/or various buffers.

It will be appreciated that the pharmaceutical compositions of the invention may include ions and a defined pH for potentiation of action of the active agent. Additionally, the compositions may be subjected to conventional pharmaceutical operations such as sterilisation and/or may contain conventional adjuvants such as preservatives, stabilisers, wetting agents, emulsifiers, buffers, fillers, etc.

The pharmaceutical compositions according to the invention may be administered via any suitable route known to those skilled in the art. Thus, possible routes of administration include parenteral (intravenous, subcutaneous, and intramuscular), topical, ocular, nasal, pulmonar, buccal, oral, parenteral, vaginal and rectal. Also administration from implants is possible.

Advantageously, the pharmaceutical composition is suitable for administration at or near the site of a tumour, e.g. intra-tumourally or peri-tumourally.

It is preferred that the pharmaceutical composition is suitable for parenteral administration. Methods for formulating an antibody into a pharmaceutical composition will be well-known to those skilled in the arts of medicine and pharmacy. Preferred compositions are described in the accompanying Examples.

The combination therapy of the invention may be delivered using an injectable sustained-release drug delivery system. These are designed specifically to reduce the frequency of injections. An example of such a system is Nutropin Depot which encapsulates recombinant human growth hormone (rhGH) in biodegradable microspheres that, once injected, release rhGH slowly over a sustained period. Preferably, delivery is performed intra-muscularly (i.m.) and/or sub-cutaneously (s.c.) and/or intravenously (i.v.).

The combination therapy of the invention can be administered by a surgically implanted device that releases the drug directly to the required site. For example, Vitrasert releases ganciclovir directly into the eye to treat CMV retinitis. The direct application of this toxic agent to the site of disease achieves effective therapy without the drug's significant systemic side-effects.

Electroporation therapy (EPT) systems can also be employed for the administration of the combination therapy of the invention. A device which delivers a pulsed electric field to cells increases the permeability of the cell membranes to the drug, resulting in a significant enhancement of intracellular drug delivery.

The combination therapy of the invention can also be delivered by electro-incorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with drugs or genes or can simply act as "bullets" that generate pores in the skin through which the drugs can enter.

An alternative combination therapy of the invention is the ReGel injectable system that is thermo-sensitive. Below body temperature, ReGel is an injectable liquid while at body temperature it immediately forms a gel reservoir that slowly erodes and dissolves into known, safe, biodegradable polymers. The active substance is delivered over time as the biopolymers dissolve.

The combination therapy of the invention can also be delivered orally. The process employs a natural process for oral uptake of vitamin $B_{12}$ and/or vitamin D in the body to co-deliver proteins and peptides. By riding the vitamin $B_{12}$ and/or vitamin D uptake system, the agents, medicaments and pharmaceutical compositions of the invention can move through the intestinal wall. Complexes are synthesised between vitamin $B_{12}$ analogues and/or vitamin D analogues and the drug that retain both significant affinity for intrinsic factor (IF) in the vitamin $B_{12}$ portion/vitamin D portion of the complex and significant bioactivity of the active substance of the complex.

The combination therapy of the invention can be introduced to cells by "Trojan peptides". These are a class of polypeptides called penetratins which have translocating properties and are capable of carrying hydrophilic compounds across the plasma membrane. This system allows direct targeting of oligopeptides to the cytoplasm and nucleus, and may be non-cell type specific and highly efficient. See Derossi et al. (1998), Trends Cell Biol. 8, 84-87.

Preferably, the combination therapy of the invention is a unit dosage containing a daily dose or unit, daily sub-dose or an appropriate fraction thereof, of the active ingredient.

The combination therapy of the invention will normally be administered orally or by any parenteral route, in the form of a pharmaceutical composition comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the combination therapy of the invention can be administered alone but will generally be administered in admixture with a suitable pharmaceutical excipient, diluent or carrier selected with regard to the intended route of administration and standard pharmaceutical practice.

For example, the combination therapy of the invention can be administered orally, buccally or sublingually in the form of tablets, capsules, ovules, elixirs, solutions or suspensions, which may contain flavouring or colouring agents, for immediate-, delayed- or controlled-release applications. The agents, medicaments and pharmaceutical compositions of the invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, cellulose, milk sugar or high molecular weight polyethylene glycols. For aqueous suspensions and/or elixirs, the agents, medicaments and pharmaceutical compositions of the invention may be combined with various sweetening or flavouring agents, colouring matter or dyes, with emulsifying and/or suspending agents and with diluents such as water, ethanol, propylene glycol and glycerin, and combinations thereof.

The combination therapy of the invention can be administered parenterally, for example, intravenously, intra-arterially, intraperitoneally, intra-thecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Medicaments and pharmaceutical compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The medicaments and pharmaceutical compositions may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

The combination therapy of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active agent, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of an agent of the invention and a suitable powder base such as lactose or starch.

Alternatively, the combination therapy of the invention can be administered in the form of a suppository or pessary, or they may be applied topically in the form of a lotion, solution, cream, gel, ointment or dusting powder. The agents, medicaments and pharmaceutical compositions of the invention may also be transdermally administered, for example, by the use of a skin patch. They may also be administered by the ocular route, particularly for treating diseases of the eye.

For ophthalmic use, the combination therapy of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the combination therapy of the invention can be formulated as a suitable ointment containing the active agent suspended or dissolved in, for example, a mixture with one or more of the following: mineral oil, liquid petrolatum, white petrolatum, propylene glycol, polyoxyethylene polyoxypropylene agent, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Generally, in humans, local administration of the combination therapy of the invention at or near the site of a tumour is the preferred route, in particular intra-tumoural or peri-tumoural administration.

For veterinary use, the combination therapy of the invention is administered as a suitably acceptable formulation in accordance with normal veterinary practice and the veterinary surgeon will determine the dosing regimen and route of administration which will be most appropriate for a particular animal.

Embodiments of the invention include, but are not limited to, the following:

A. A method for treating a solid tumour in a subject, the method comprising (a) administering to the subject a therapeutically effective amount of an antibody, or antigen binding portion thereof, that specifically binds to CD40 and that is retained at the tumour site following administration, and optionally (b) systemically administering to the subject a therapeutically effective amount of an additional therapeutic agent.

B. The method according to Embodiment A wherein the additional therapeutic agent of step (b) is an immunotherapeutic agent for the treatment of cancer which is not an anti-CD40 antibody.

C. The method according to Embodiment b wherein said immunotherapeutic agent is a PD1 inhibitor, optionally wherein said PD1 inhibitor is an anti-PD1 or an anti-PD-L1 antibody.

D. The method according to any one of the preceding Embodiments wherein the solid tumour is an adenoma, a blastoma, a carcinoma, a desmoid tumour, a desmopolastic small round cell tumour, an endocrine tumour, a germ cell tumour, a lymphoma, a sarcoma, a Wilms tumour, a lung tumour, a colon tumour, a lymph tumour, a breast tumour or a melanoma.

E. The method according to any one of the preceding Embodiments wherein the solid tumour is a melanoma, preferably a metastatic melanoma.

F. The method according to any one of the preceding Embodiments, wherein the antibody of step (a) comprises at least one CDR selected from SEQ ID NOs 1, 2, 3, 4, 5 and 6.

G. The method according to any one of the preceding Embodiments, wherein the antibody of step (a) comprises the CDR sequences of SEQ ID NOs: 1, 2 and 3 and/or SEQ ID NOs: 4, 5 and 6.

H. The method according to any one of the preceding Embodiments, wherein the antibody of step (a) comprises the light chain variable region of SEQ ID NO: 7 and/or the heavy chain variable region of SEQ ID NO: 8.

I. The method according to any one of the preceding Embodiments, wherein the antibody of step (a) comprises the light chain constant region of SEQ ID NO: 11 and/or the heavy chain constant region of SEQ ID NO: 12.

J. The method according to any one of the preceding Embodiments, wherein the antibody of step (a) competes for binding to human CD40 with an antibody which comprises the light chain variable region of SEQ ID NO: 7 and the heavy chain variable region of SEQ ID NO: 8.

K. The method according to any one of the preceding Embodiments wherein steps (a) and (b) are carried out simultaneously or wherein step (b) is carried out between 24 hours and two weeks after step (a), between 24 hours and one week after step (a), between 24 and 72 hours after step (a), or between 24 and 48 hours after step (a).

L. The method according to any one of the preceding Embodiments wherein step (a) comprises local administration of the antibody to the tumour site, optionally wherein the antibody is formulated as a composition suitable for local administration with at least one pharmaceutically acceptable diluent or carrier, and/or the antibody is conjugated to an additional therapeutic moiety.

M. The method according to any one of the preceding Embodiments, wherein at least 30% of the amount of antibody administered in step (a) is retained at the tumour site at four hours after administration, preferably wherein at least 40% of the said amount is retained at the tumour site at four hours after administration.

N. The method according to any one of the preceding Embodiments wherein the additional therapeutic agent of step (b) is formulated as a composition suitable for systemic administration with at least one pharmaceutically acceptable diluent or carrier.

O. The method according to one of the preceding Embodiments wherein step (a) is conducted on multiple separate occasions and step (b) is conducted such that exposure of the subject to the additional therapeutic agent is continuous for the duration of the method.

P. The method according to any one of the preceding Embodiments wherein the subject is a human.

Q. A kit for treating a solid tumour in a subject, the kit comprising (a) a therapeutically effective amount of an antibody that specifically binds to CD40 and that is retained at the tumour site following administration and optionally (b) a therapeutically effective amount of an additional therapeutic agent that is suitable for systemic administration to a subject.

R. An antibody, or antigen binding portion thereof, that specifically binds to CD40 and that is capable of being retained at the tumour site following administration, for use in treating a solid tumour in a subject.

S. An antibody, or antigen binding portion thereof, according to Embodiment R for use in combination with one or more additional therapeutic agents, wherein the additional therapeutic agent(s) is/are not an anti-CD40 antibody.

T. An antibody, or antigen binding portion thereof, according to Embodiment S wherein said additional therapeutic agent is a cancer treatment selected from the group consisting of a conventional radiotherapeutic, a pathway inhibitor (such as a tyrosine kinase inhibitor or Serine/threonine kinase inhibitor), a cytokine (such as IL-2, IL-12, IL-15 or IL-21), a chemotherapeutic agent and an immunotherapeutic agent.

U. An antibody, or antigen binding portion thereof, according to claim Embodiment S or T for use in combination with one or more of the following additional therapeutic agents:
 (i) an anti-PD1 immunotherapeutic agent;
 (ii) an anti-CTLA-4 immunotherapeutic agent;
 (iii) an anti-OX40 immunotherapeutic agent; and/or
 (iv) an anti-CD137 immunotherapeutic agent.

V. An antibody, or antigen binding portion thereof, according to Embodiment T or U wherein said immunotherapeutic agent is a PD1 inhibitor, optionally wherein said PD1 inhibitor is an anti-PD1 or an anti-PD-L1 antibody.

W. An antibody, or antigen binding portion thereof, according to any one of Embodiments R to V wherein the solid tumour is an adenoma, a blastoma, a carcinoma, a desmoid tumour, a desmopolastic small round cell tumour, an endocrine tumour, a germ cell tumour, a lymphoma, a sarcoma, a Wilms tumour, a lung tumour, a colon tumour, a lymph tumour, a breast tumour or a melanoma.

X. An antibody, or antigen binding portion thereof, according to any one of Embodiments R to W wherein the solid tumour is a melanoma, preferably a metastatic melanoma.

Y. An antibody, or antigen binding portion thereof, according to any one of Claims Embodiments R to X comprising at least one CDR selected from SEQ ID NOs 1, 2, 3, 4, 5 and 6.

Z. An antibody, or antigen binding portion thereof, according to any one of Embodiments R to Y comprising the CDR sequences of SEQ ID NOs: 1, 2 and 3 and/or SEQ ID NOs: 4, 5 and 6.

AA. An antibody, or antigen binding portion thereof, according to any one of Embodiments R to Z comprising the light chain variable region of SEQ ID NO: 7 and/or the heavy chain variable region of SEQ ID NO: 8.

BB. An antibody, or antigen binding portion thereof, according to any one of Embodiments R to AA comprising the light chain constant region of SEQ ID NO: 11 and/or the heavy chain constant region of SEQ ID NO: 12

CC. An antibody, or antigen binding portion thereof, according to any one of Embodiments R to BB wherein the antibody, or antigen binding portion thereof, competes for binding to human CD40 with an antibody which comprises the light chain variable region of SEQ ID NO: 7 and the heavy chain variable region of SEQ ID NO: 8.

DD. An antibody, or antigen binding portion thereof, according to any one of Embodiments R to CC wherein the antibody is formulated as a composition suitable for local administration with at least one pharmaceutically acceptable diluent or carrier, and/or the antibody is conjugated to an additional therapeutic moiety.

EE. A combination therapy composition comprising an antibody, or antigen binding portion thereof, according to any one of Embodiments R to DD and one or more additional therapeutic agent(s), wherein the additional therapeutic agent(s) is/are not an anti-CD40 antibody.

FF. A combination therapy composition according to Embodiment EE wherein said additional therapeutic agent is a cancer treatment selected from the group consisting of a conventional radiotherapeutic, a pathway inhibitor (such as a tyrosine kinase inhibitor or Serine/threonine kinase inhibitor), a cytokine (such as IL-2, IL-12, IL-15 or IL-21), a chemotherapeutic agent and an immunotherapeutic agent.

GG. A combination therapy composition according to Embodiments EE or FF comprising:
 (i) an anti-PD1 immunotherapeutic agent;
 (ii) an anti-CTLA-4 immunotherapeutic agent;
 (iii) an anti-OX40 immunotherapeutic agent; and/or
 (iv) an anti-CD137 immunotherapeutic agent.

HH. A combination therapy composition according to any one of Embodiments EE to GG wherein said immunotherapeutic agent is a PD1 inhibitor, optionally wherein said PD1 inhibitor is an anti-PD1 or an anti-PD-L1 antibody.

II. Use of an antibody, or antigen binding portion thereof, as defined in any one of Embodiments R to DD in the preparation of a medicament for the treatment of a solid tumour in a subject.

The present invention is further illustrated by the following examples which should not be construed as further limiting. The contents of all figures and all references, patents and published patent applications cited throughout this application are expressly incorporated herein by reference.

EXAMPLES

Example 1

Sequence Information

Anti-CD40 Antibody Clone G12 (Antibody ADC-1013)

(a) CDR Sequences (Defined According to the IMGT Numbering, with Core CDR Sequences Underlined Therein)

| | | |
|---|---|---|
| V<sub>L</sub> CDR1: | CTGS<u>SSNIGAGYN</u>VY; | [SEQ ID NO: 1] |
| V<sub>L</sub> CDR2: | <u>GNINRPS</u>; | [SEQ ID NO: 2] |
| V<sub>L</sub> CDR3: | <u>CAAWDKSISGLV</u>; | [SEQ ID NO: 3] |
| V<sub>H</sub> CDR1: | <u>GFTFSTYGMH</u>; | [SEQ ID NO: 4] |
| V<sub>H</sub> CDR2: | GKGLEWLSY<u>ISGGSSYI</u>FYADSVRGR; | [SEQ ID NO: 5] |
| V<sub>H</sub> CDR3: | <u>CARILRGGSGMDL</u> | [SEQ ID NO: 6] |

(b) Variable Region Sequences

```
Variable light chain (V_L) amino acid sequence -
                                           SEQ ID NO: 7
QSVLTQPPSASGTPGQRVTISCTGSSSNIGAGYNVYWYQQLPGTAPKLLI
YGNINRPSGVPDRFSGSKSGTSASLAISGLRSEDEADYYCAAWDKSISGL
VFGGGTKLTVLG Variable heavy chain (V_H) amino acid sequence -
                                           SEQ ID NO: 8
EVQLLESGGGLVQPGGSLRLSCAASGFTFSTYGMHWVRQAPGKGLEWLSY
ISGGSSYIFYADSVRGRFTISRDNSENALYLQMNSLRAEDTAVYYCARIL
RGGSGMDLWGQGTLVTVSS Variable light chain (V_L) nucleotide sequence -
                                           SEQ ID NO: 9
CAGTCTGTGCTGACTCAGCCACCCTCAGCGTCTGGGACCCCCGGGCAGAG
GGTCACCATCTCTTGCACTGGGAGCAGCTCCAACATCGGGGCGGGTTACA
ATGTATACTGGTATCAGCAGCTCCCAGGAACGGCCCCCAAACTCCTCATC
TATGGTAACATCAATCGGCCCTCAGGGGTCCCTGACCGATTCTCTGGCTC
CAAGTCTGGCACCTCAGCCTCCCTGGCCATCAGTGGGCTCCGGTCCGAGG
ATGAGGCTGATTATTACTGTGCAGCATGGGATAAGAGCATTTCTGGTCTG
GTTTTCGGCGGAGGAACCAAGCTGACGGTCCTAGGT Variable heavy chain (V_H) nucleotide sequence -
                                          SEQ ID NO: 10
GAGGTGCAGCTGTTGGAGTCTGGGGGAGGCTTGGTACAGCCTGGGGGGTC
CCTGAGACTCTCCTGTGCAGCCTCTGGATTCACCTTCAGTACTTATGGCA
TGCACTGGGTCCGCCAGGCTCCAGGGAAGGGGCTGGAGTGGCTTTCATAT
ATTAGTGGTGGTAGTAGTTACATTTTCTACGCAGACTCAGTGAGGGCCG
ATTCACCATCTCCAGAGACAACTCCGAGAACGCGCTGTATCTGCAAATGA
ACAGCCTGAGAGCCGAGGACACGGCCGTGTATTACTGTGCGAGAATATTA
AGAGGCGGGAGCGGTATGGACCTCTGGGGCCAAGGTACACTGGTCACCGT
GAGCTCA
```

(c) Exemplary Constant Region Amino Acid Sequences

```
Human Ig lambda light chain C2 region
(NCBI AAA59107.1) -
                                          SEQ ID NO: 11
QPKAAPSVTLFPPSSEELQANKATLVCLISDFYPGAVTVAWKADSSPVKA
GVETTTPSKQSNNKYAASSYLSLTPEQWKSHRSYSCQVTHEGSTVEKTVA
PTECS Human Ig gamma-1 heavy chain constant region
(Uniprot P01857.1) -
                                          SEQ ID NO: 12
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK Human CD40 Sequence -
                                          SEQ ID NO: 13
>gi|117606560|gb|ABK41937.1| CD40 molecule, TNF
receptor superfamily member 5 [Homo sapiens]
MVRLPLQCVLWGCLLTAVHPEPPTACREKQYLINSQCCSLCQPGQKLVSD
CTEFTETECLPCGESEFLDTWNRETHCHQHKYCDPNLGLRVQQKGTSETD
TICTCEEGWHCTSEACESCVLHRSCSPGFGVKQIATGVSDTICEPCPVGF
FSNVSSAFEKCHPWTSCETKDLVVQQAGTNKTDVVCGPQDRLRALVVIPI
IFGILFAILLVLVFIKKVAKKPTNKAPHPKQEPQEINFPDDLPGSNTAAP
VQETLHGCQPVTQEDGKESRISVQERQ
```

Example 2

Bioavailability After Local or Systemic Administration

Preclinical studies were performed in cynomolgus monkey, and mice, in order to study the bioavailability of ADC-1013 after peritumoral, intratumoral or intravenous administration.

Material and Methods

The pharmacokinetics of ADC-1013 was assessed in a human CD40 positive transgenic mouse model inoculated with human CD40 negative bladder cancer cells, MB49. ADC-1013 was injected intratumorally (IT), peritumorally (PT) or intravenously (IV) at a dose of 100 µg, and serum was collected pre-treatment and 4 and 24 h post treatment. The pharmacokinetic profile (FIG. 1) indicates that the systemic exposure at of ADC-1013 at 4 hours post administration is reduced 100 to 1000-fold after IT or PT administration as compared to IV.

Cynomolgus monkeys were exposed to ADC-1013 via the subcutaneous or the intravenous route. Sub-cutaneous administration here is analogous to local administration to a melanoma.

Results and Conclusions

Figure 2:
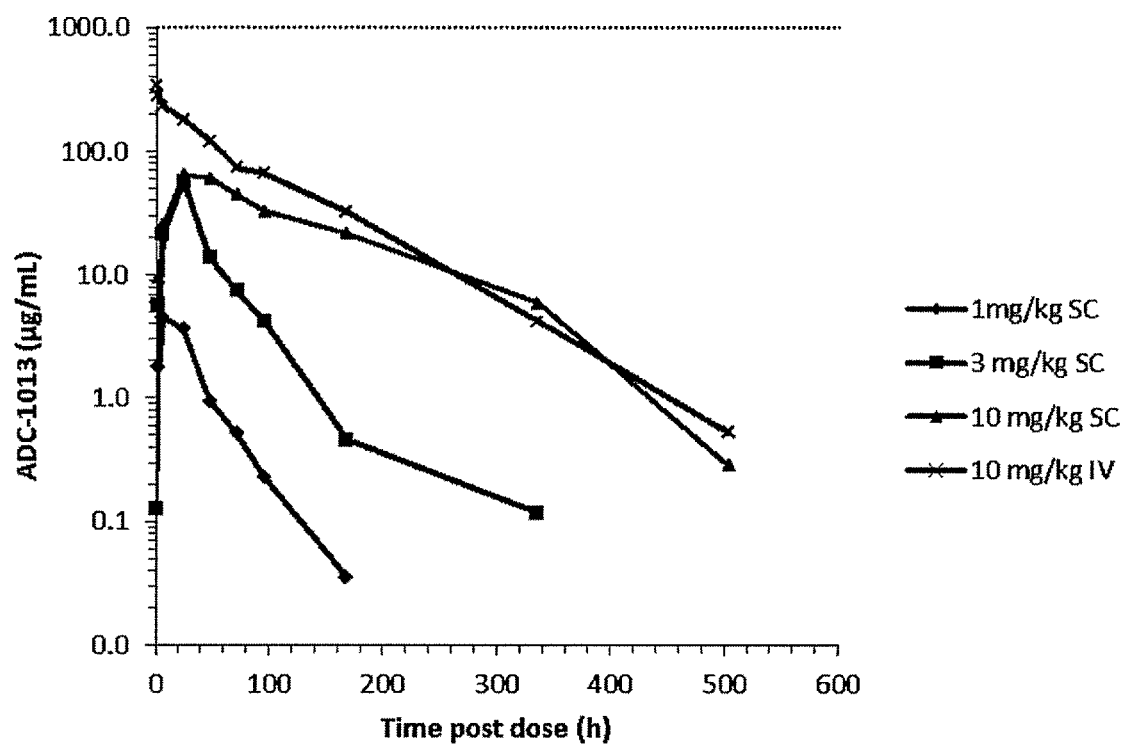
FIG. 2 shows the level of antibody detectable in blood samples of Cynomolgus monkeys after administration of antibody at the indicated doses via the subcutaneous or the intravenous route.

Blood samples were taken from all animals for toxicokinetic analysis at the following timepoints: Pre-dose and at 15 minutes and 2, 6, 24, 48, 72, 96 and 168 hours post-dose and levels of ADC1013 measured (FIG. 2). The bioavailability of ADC1013 after subcutaneous administration, based on mean area-under the curve (AUC-96) was calculated. The AUC-96 for subcutaneous vs intravenous administration ranged between 28-42% indicating 28%-42% systemic bioavailability.

These observations were applied in deciding dose levels of administered combinations of immunotherapeutic antibodies in the B16.F10 mouse model as disclosed in Example 3.

Example 3

In Vivo Murine Melanoma Model

B16.F10 is the tumor cell line that is most frequently used as a model for melanoma in pre-clinical mouse models (Grosso 2013 Cancer Immunity Review). The mouse B16.F10 melanoma cell line compares well to human melanomas because it expresses MHC at low levels and is considered to be poorly immunogenic (Lechner J immunother 2013). Low MHC levels may e.g. be associated with insufficient T cell activation, possibly making such tumors more difficult to treat with immunotherapy. In order to increase the translational relevance of B16.F10, the cell line was transfected with human CD40. The transfected line (referred to as B16.F10(hCD40+) was used for these experiments.

Material and Methods

The melanoma cell line B16.F10 was obtained from American Type Cell Collection (ATCC). The hCD40 expressing line B16.F10(hCD40+) was obtained by transfecting B16.F10 with linearized vector containing human CD40 and by using Lipofectamine (Invitrogen). The vector contained elements conferring Neomycin resistance. The transfected cells were cultured in DMEM (containing 4.5 g/L glucose, Ultraglutamine I, and sodiumpyruvat), 10%FCS, Hepes, and 1 mg/ml G418 to select for stable transfectants. CD40 positive clones were selected using CD40 biotin and magnetic beads (Miltenyi). A single clone with verified hCD40 expression, measured by flow cytometry, was selected (clone 5.G12.46).

The B16.F10(hCD40+), growing in log phase, was injected subcutaneously at day 0 (D0) into the right flank of hCD40 transgenic mouse (hCD40Tg) in a volume of 100 µL. The average inoculated number of cells was $0.1 \times 10^6$ per mouse. The tumor growth was measured with a digital caliper in width, length and height of which the tumor volume was calculated (w/2×l/2×h/2×pi×(4/3)). The treatments were administered at days 3, 6 and 9. ADC-1013 was administered intratumorally (20 µL, 100 µg per dose) and anti-PD-1 (Clone RPM1-14, BioXcell) intraperitoneally (100 µL, 250 µg per dose).

Results and Conclusions

Figure 3:
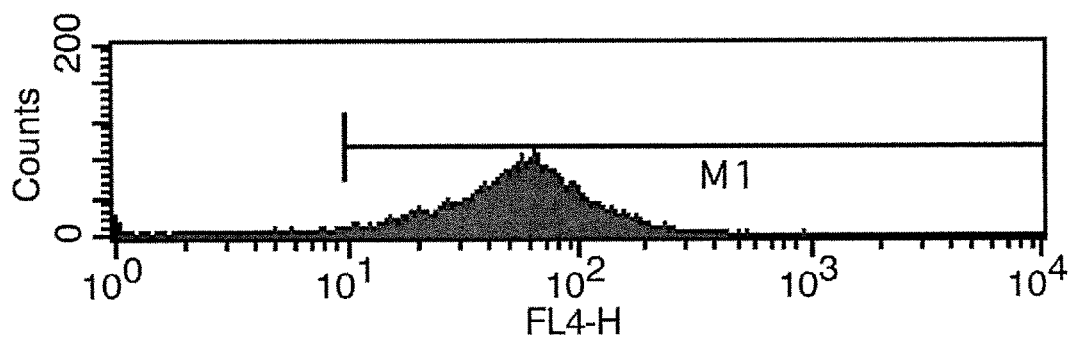
FIG. 3 shows the results of flow cytometric analysis of cell-surface human CD40 expression by (A) B16.F10 (hCD40+) clone 5.G12.46 cells and (B) mock transfected cells.
Figure 3:
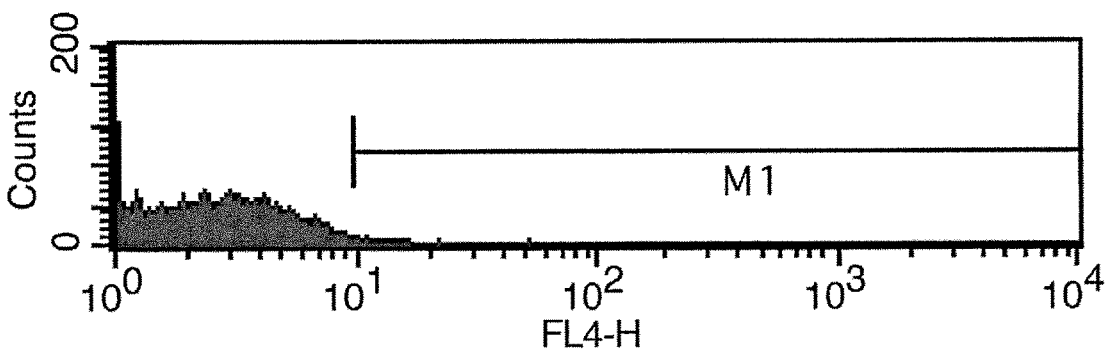
Figure 4:
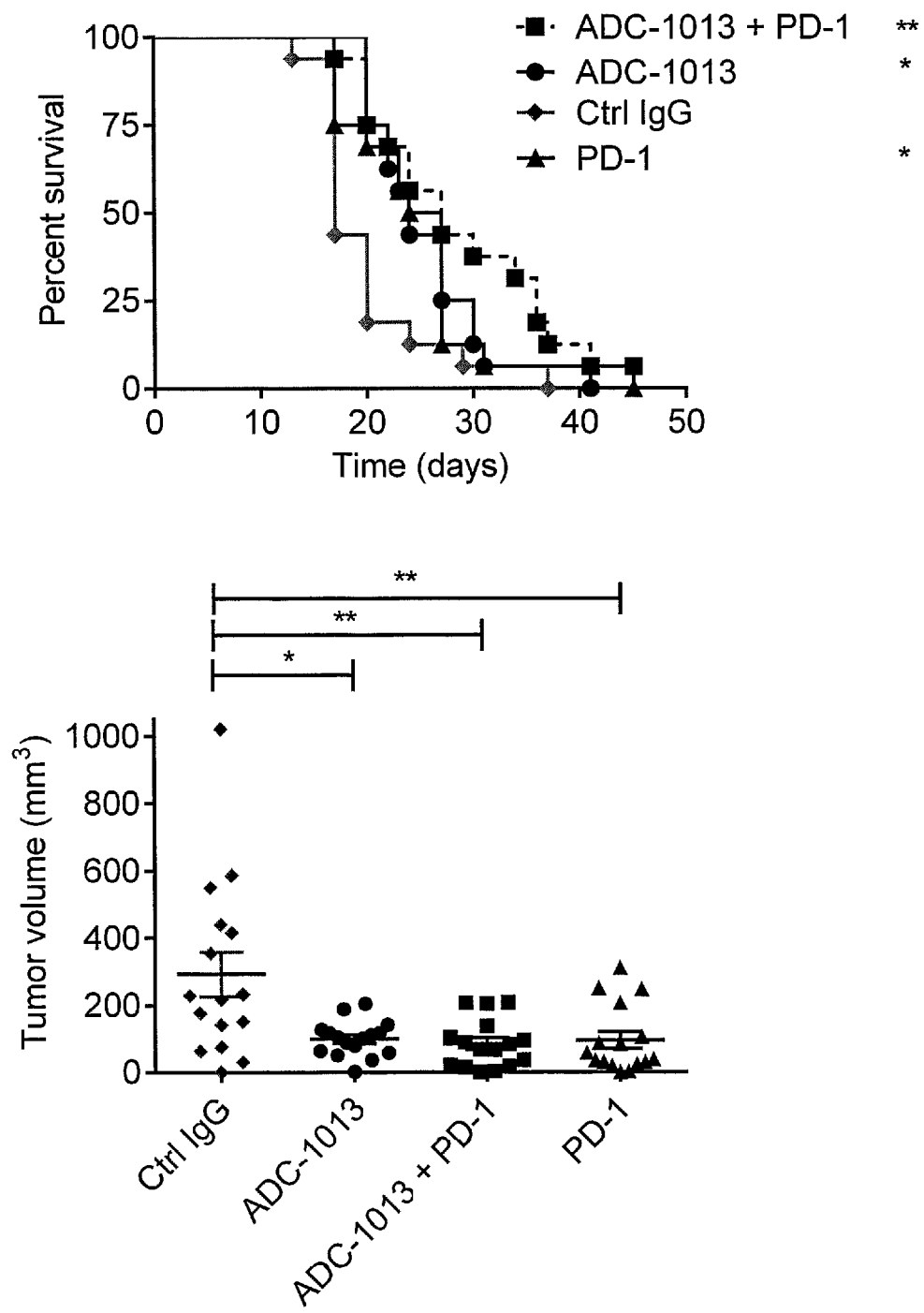
FIG. 4 (top panel) shows survival rates of hCD40tg mice bearing subcutaneous B16.F10(hCD40+) melanoma after treatment with control, ADC-1013 only, or ADC-1013 with an anti-PD-1 antibody ("PD-1").

Transfected B16.F10(hCD40+) melanoma cell line displayed substantial expression of human CD40, as shown in FIG. 3A. The anti-tumor effects of ADC-1013 were determined in hCD40tg mice bearing subcutaneous B16.F10 (hCD40+) melanoma by survival (FIG. 4, top panel) and tumor volume at the day where the first mouse was sacrificed (FIG. 4 bottom panel). ADC-1013 displayed significant degrease of tumor growth measured by increased survival time and decreased tumor volume. The anti-tumor efficacy was increased by treating the animals with a combination of ADC-1013 and an anti-PD-1 antibody.

Example 4

In Vivo Murine Bladder Cancer Model

Material and Methods

MB49 bladder cancer cells were used to initiate tumors on 8-week-old female hCD40Tg mice. On day 0, $0.25 \times 10^6$ tumor cells were inoculated subcutaneously into the right flank of the mouse. On day 14, mice were injected either intratumorally or intraperitoneally with a test anti-CD40 antibody (total of 1 ug and 30 ug of antibody per mouse, or PBS; 4 mice per group). On day 16, 40 mice were sacrificed by cervical dislocation. Tumor-draining lymph nodes were collected into full media, and two tumors or lymph nodes from each experimental group were pooled together. Collected tissue was homogenized enzymatically and mechanically using Liberase TL (Roche) and nylon net filters (100 µm; Fischer Scientific). Membranes were thoroughly washed with RPMI media containing 3-10 mM EDTA and 0.1% fetal calf serum to prepare single-cell suspensions. Isolated cells were washed in PBS containing 0.5% bovine serum albumin, and unspecific Fc-binding was blocked by treating cells with mouse anti-CD16/32 (BD Bioscience).

CD86 expression levels (as a marker for activation) were separately analysed on CD11c-positive cells and CD11b-positive cells by flow cytometry. CD11c is a marker for dendritic cells. CD11b is expressed on monocytes, macrophages and subsets of dendritic cells. Cells were stained with the live/dead fixable stain FVS450 (BD Bioscience) and antibodies specific for CD11c-PE, CD11b-PECy7 and CD86-APC (BD Bioscience) diluted 1:100. After staining all cells were paraformaldehyde fixed using Cellfix (BD Bioscience). Staining for each sample was measured and calculated as CD86 (sample)-FMO(sample) and presented as % positive cells minus PBS control. Stained cells were analyzed using FACS Verse (Becton Dickinson) and FlowJo vX analysis software. The results are shown in FIGS. 5A (CD11c cells) and 5B (CD11b cells).

Results and Conclusions

Figure 5A:
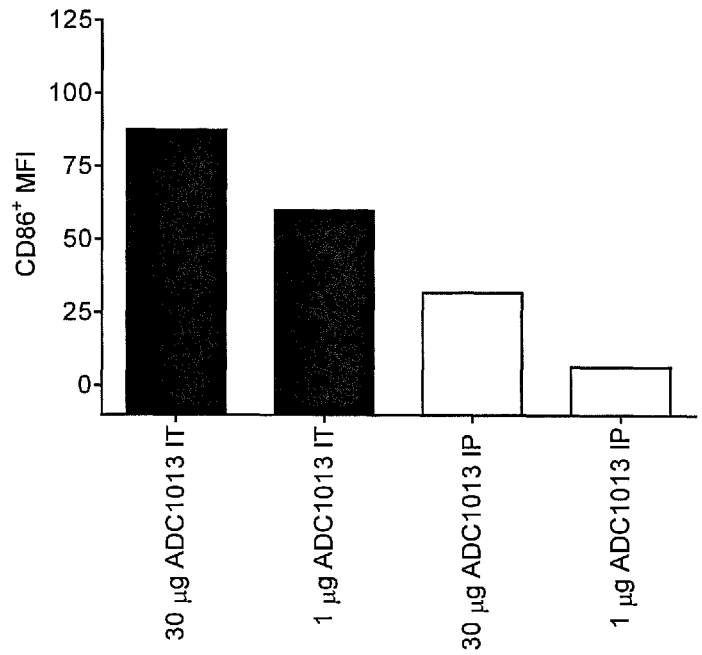
FIG. 5A shows the results of an assay for the activation of CD11c positive cells in the draining lymph nodes after different modes of administration of an anti-CD40 antibody in a mouse tumour model. Intratumoral administration (IT), intraperitoneal administration (IP). Activation is indicated by CD86 expression level, measured by mean fluorescent intensity (MFI).
Figure 5B:
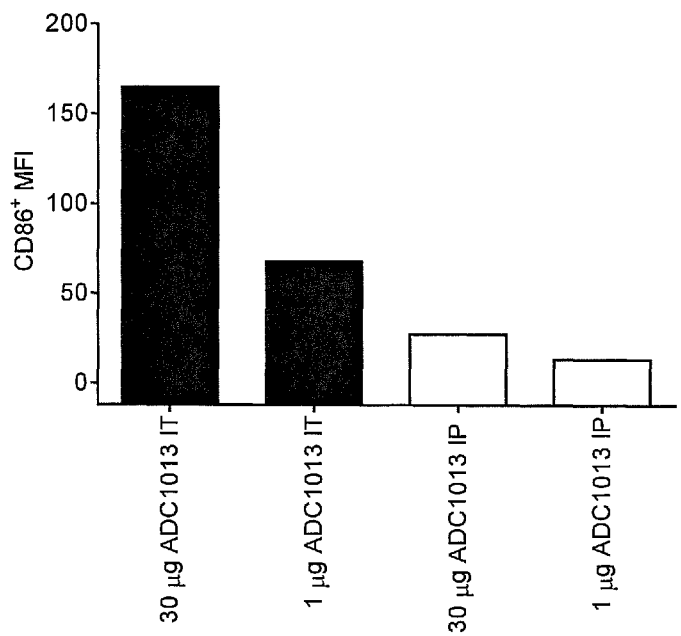
FIG. 5B shows the results of an assay for the activation of CD11b positive cells in the draining lymph nodes after different modes of administration of an anti-CD40 antibody in a mouse tumour model. Intratumoral administration (IT), intraperitoneal administration (IP). Activation is indicated by CD86 expression level, measured by mean fluorescent intensity (MFI).

The data in FIG. 5A shows that treatment with anti-CD40 antibody increased the activation of dendritic cells measured by CD86 expression in the tumor. The data in FIG. 5B shows that treatment with anti-CD40 antibody increased the activation of CD11b positive cells measured by CD86 expression in the tumor. Overall, a stronger activation is obtained following intratumoral (IT) treatment compared to intraperitoneal (IP) treatment. Treatment with a low dose of 1 µg given intratumourally (IT) generated an unexpectedly high activation of dendritic cells.

Example 5

In Vivo Effect of Combination Therapy I

Material and Methods

Figure 6:
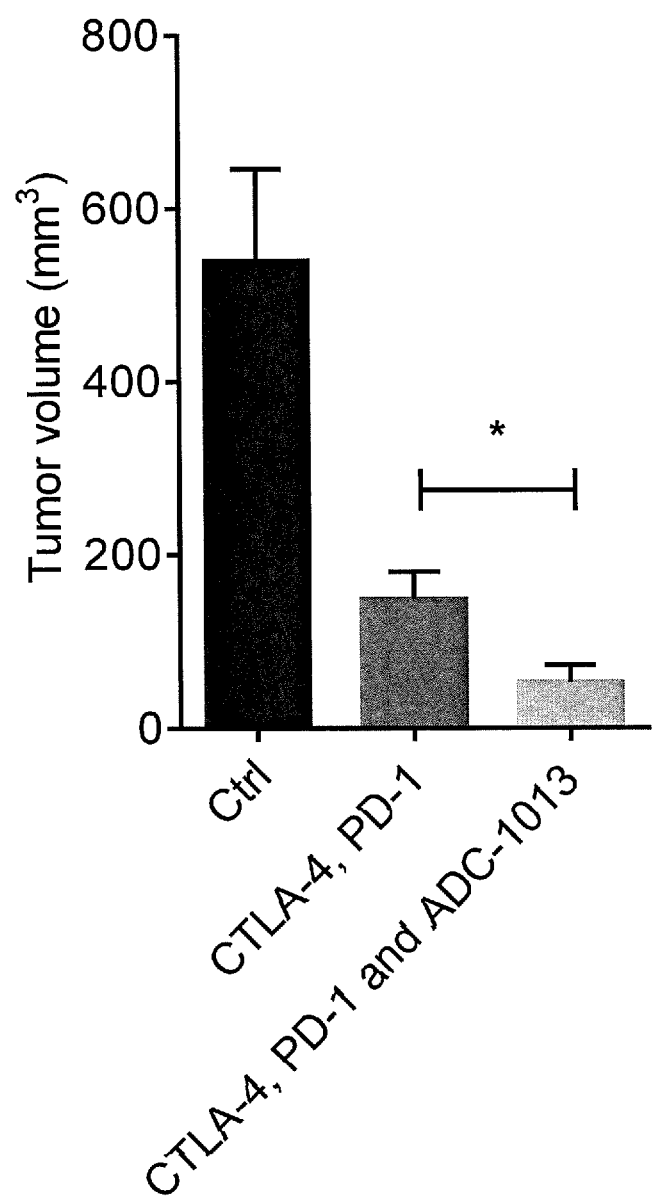
FIG. 6. B16.F10.hCD40+ tumors were inoculated on one flank. The treatments were administered at days 3, 6 and 9. ADC-1013 was administered intratumorally (100 µg per dose). Anti-PD-1, 250 µg per dose (Clone RPM1-14, BioXcell) and anti-CTLA-4 antibody, 100 µg per dose (9D9, BioXcel) was injected intraperitoneally. The tumor volume at day 14 is shown.

The B16.F10(hCD40+) tumor cell line, growing in log phase, was injected subcutaneously at day 0 (D0) into the right flank of hCD40 transgenic mouse (hCD40Tg) in a volume of 100 µL. The number of inoculated cells was $0.1 \times 10^6$ per mouse. The tumor growth was measured with a digital callipher in width, length and height of which the tumor volume was calculated (w/2×l/2×h/2×pi×(4/3)). The treatments were administered at days 3, 6 and 9. ADC-1013 was administered intratumorally (100 µg per dose). Anti-PD-1, 250 µg per dose (Clone RPM1-14, BioXcell) and anti-CTLA-4 antibody, 100 μg per dose (9D9, BioXcel) was injected intraperitoneally. The tumor volume at day 14 is shown in FIG. 6.

Results and Conclusions

It has been shown that treatment with an antibody targeting PD-1 in combination with an antibody targeting CTLA-4 may confer additive effects in clinical trials (Wolchok et al New Eng J Med, 2013). In this example, we disclose pre-clinical data suggesting that addition of treatment with ADC-1013 to the CTLA-4/PD-1 combination could further increase the therapeutic effects in melanoma patients. The anti-tumor effect measured by a decrease in tumor volume at day 14 was significantly better for CTLA-4, PD-1 and ADC-1013 compared to CTLA-4 and PD-1 alone (FIG. 6).

In a clinical setting, the CTLA-4 antibody could be any of ipilimumab, tremelimumab or other CTLA-4 targeting antibodies. The PD-1 targeting antibody could be an antibody binding to human PD-1 such as nivolumab or pembrolizumab or others. It could also be an antibody that binds to the ligands of PD-1, such as PD-L1 and PD-L2 targeting antibodies, such as durvalumab and avelumab.

Example 6

In Vivo Effect of Combination Therapy II

Material and Methods

Figure 7:
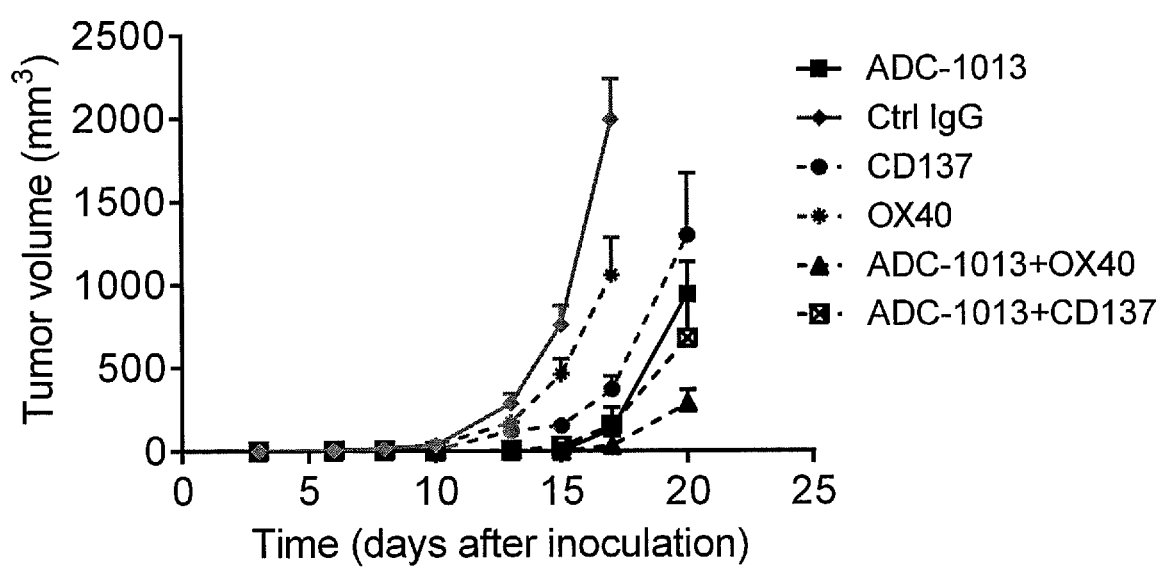
FIG. 7. B16.F10 tumors were inoculated on one flank. The treatments were administered at days 3, 6 and 9. ADC-1013, anti-CD137 (Lob 12.3) and anti-OX40 (CD86) antibodies and controls was administered intratumorally (100 µg per dose). The tumor volume was followed over time.

The B16.F10 tumor cell line, growing in log phase, was injected subcutaneously at day 0 (D0) into the right flank of hCD40 transgenic mouse (hCD40Tg) in a volume of 100 μl. The number of inoculated cells was $0.1 \times 10^6$ per mouse. The tumor growth was measured with a digital calliper in width, length and height of which the tumor volume was calculated (w/2×l/2×h/2×pi×(4/3)). The treatments were administered at days 3, 6 and 9. ADC-1013, anti-CD137 (clone Lob 12.3) and anti-OX40 (CD86) antibodies and controls was administered intratumorally (100 μg per dose). The volume was followed over time as shown in FIG. 7

Results and Conclusions

Treatment with ADC-1013 generated a significant anti-tumor response compared to the control. The anti-tumor effect was greater than the anti-tumor effect obtained with antibodies targeting CD137 and OX40 (FIG. 7). The combination of ADC-1013 and OX40 resulted as well as the combination of ADC-103 with CD137 resulted in stronger anti-tumor effect compared to the monotherapies. This indicates that combining CD40 and CD137 or combining CD40 and OX40 will have clinical benefits.

Example 7

Effect of ADC-1013 on Wildtype B16 Melanoma in Mice

Material and Methods

B16.F10.hCD40+ cells or B16.F10 (wt) cells ($1 \times 10^5$) were inoculated subcutaneously, and the mice were treated intratumorally with ADC-1013 on day 3, 6, and 9 (100 μg per dose).

The mice used for this study were hCD40tg mice.

Results and Conclusions

Figure 8:
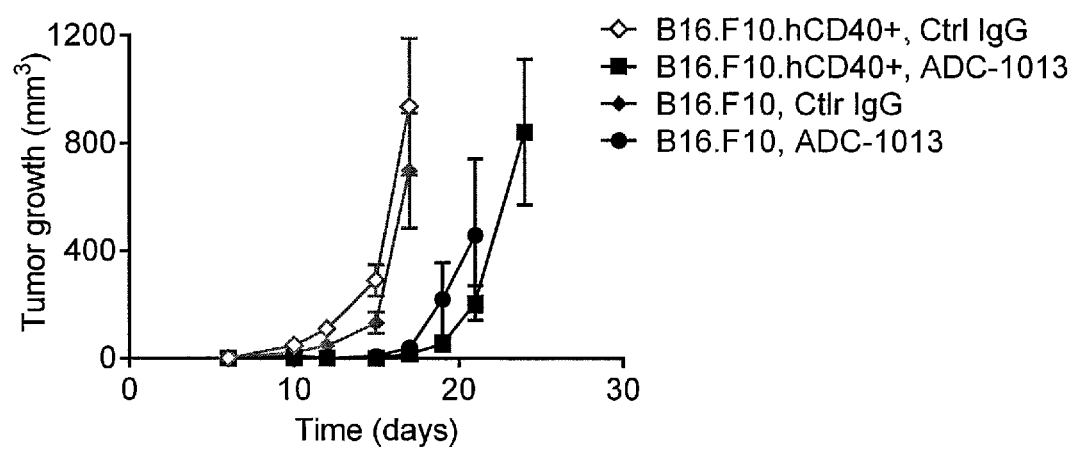
FIG. 8. Anti-tumor effect of ADC-1013 in B16.F10.hCD40+ tumor compared to the anti-tumor effect in B16.F10 (wt) tumors following treatment with ADC-1013 or control (intratumoral, 100 µg on day 3, 6 and 9).
Figure 8:
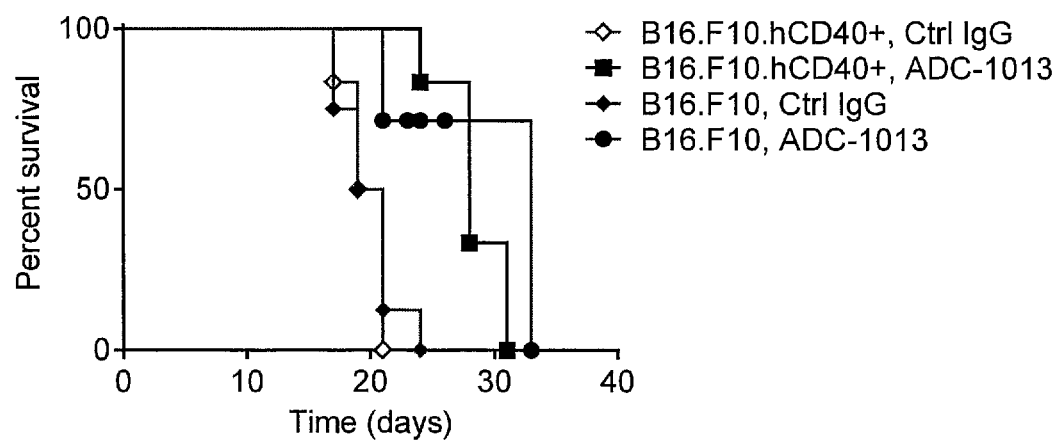

ADC-1013 generates significant anti-tumor effects also in B16.F10 tumors. The anti-tumor effect obtained in B16.F10 (wt) and B16.F10.hCD40+ tumors was similar (FIG. 8). This does not rule out that direct induction of ADCC plays a role in the treatment of human-CD40 positive melanoma. It may be that there are other qualitative differences in the hCD40 positive tumors, such as lower immune cell infiltration. Further, the human CD40 levels on the B16 tumors were low, as measured ex vivo on tumor samples.

Example 8

Effect of ADC-1013 in Lymphoma Model (A20)

Material and Methods

The A20 lymphoma cell line, growing in log phase, was injected subcutaneously at day 0 (D0) into the right flank of hCD40tg-BalbC (F1) mice in a volume of 100 μL. The hCD40tg-BalbC (F1) mice were generated by crossing hCD40tg mice with BalbC mice. The number of inoculated cells was $5 \times 10^6$ per mouse. The tumor growth was measured with a digital caliper in width, length and height of which the tumor volume was calculated (w/2×l/2×h/2×pi×(4/3)). ADC-1013 (30 μg per dose) was administered peritumorally at day 10, 13 and 16 in mice with established lymphoma tumors (A20).

Results and Conclusions

Figure 9:
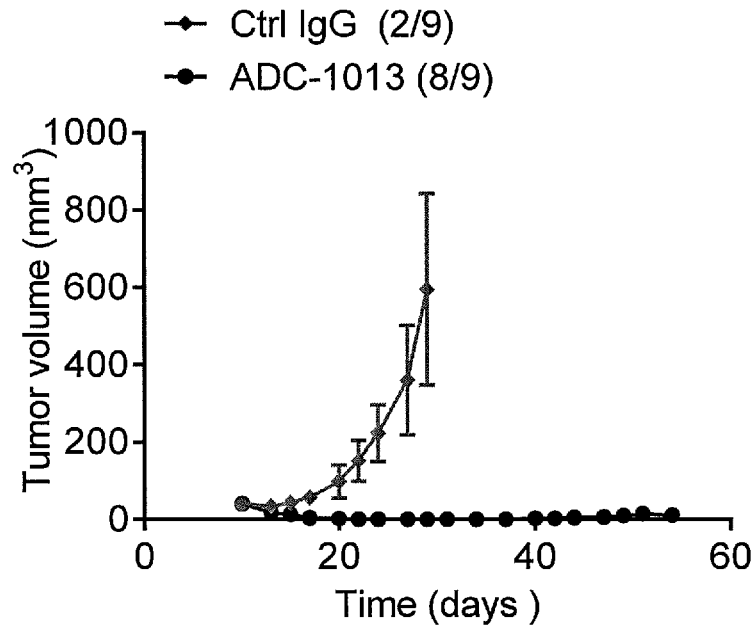
FIG. 9. ADC-1013 (30 µg) was administered intratumorally at day 10, 13, 16 in hCD40tg-BalbC (F1) mice with established lymphoma tumors (A20). Tumor volume and survival over time is presented in the figure.
Figure 9:
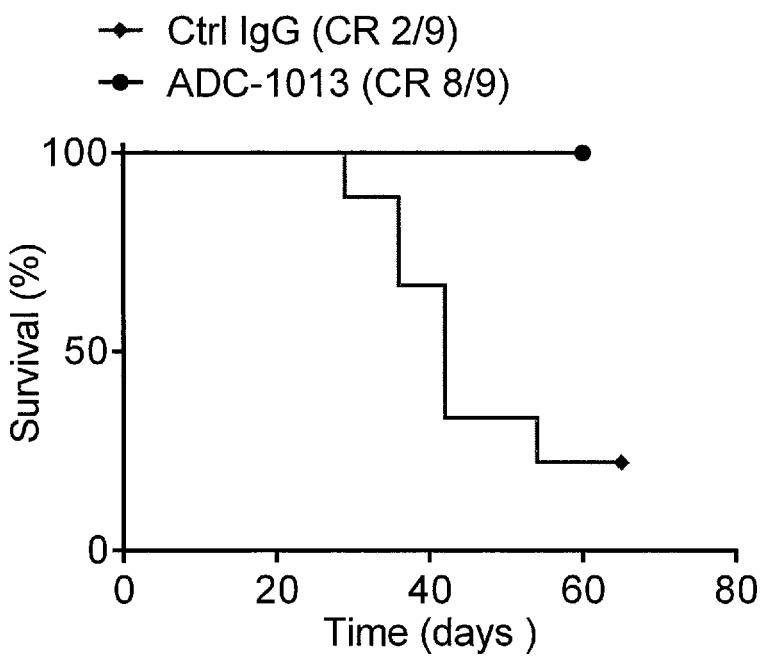

Treatment with ADC-1013 results in a significant anti-tumor effect in the A20 lymphoma model (FIG. 9). This model is hCD40 negative and so the anti-tumor effect demonstrated here is solely caused by the activation of the immune cells by ADC-1013.

Example 9

Effect of ADC-1013 in Lung Cancer Model (LLC-1)

Material and Methods

Lung cancer cell line (LLC-1) growing in log phase, was injected subcutaneously at day 0 (D0) into the right flank of hCD40tg mice in a volume of 100 μL. The number of inoculated cells was $0.25 \times 10^6$ per mouse. The tumor growth was measured with a digital calliper in width, length and height of which the tumor volume was calculated (w/2×l/2×h/2×pi×(4/3)). ADC-1013 (100 μg) was administered peritumorally at day 4, 7 and 10 in hCD40tg mice with established tumors (LLC-1).

Results and Conclusions

Figure 10:
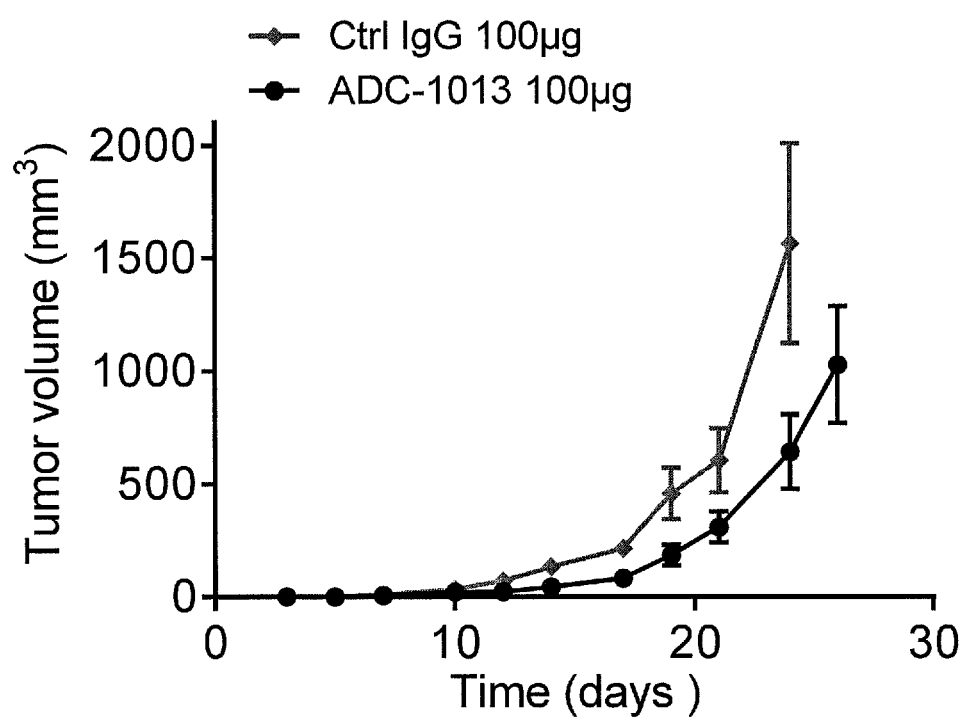
FIG. 10. ADC-1013 (100 µg) was administered intratumorally at day 4, 7 and 10 in hCD40tg mice with established tumors (LLC-1). Tumor volume over time is presented in the figure.

Treatment with ADC-1013 results in a significant ($p<0.05$, one sided Mann Whitney t test) anti-tumor effect in the lung cancer model (FIG. 10). This model is hCD40 negative and the anti-tumor effect demonstrated here is sole caused by the activation of the immune cells by ADC-1013.

Example 10

Distal Effect of Local Administration of ADC-1013

Material and Methods

Figure 11:
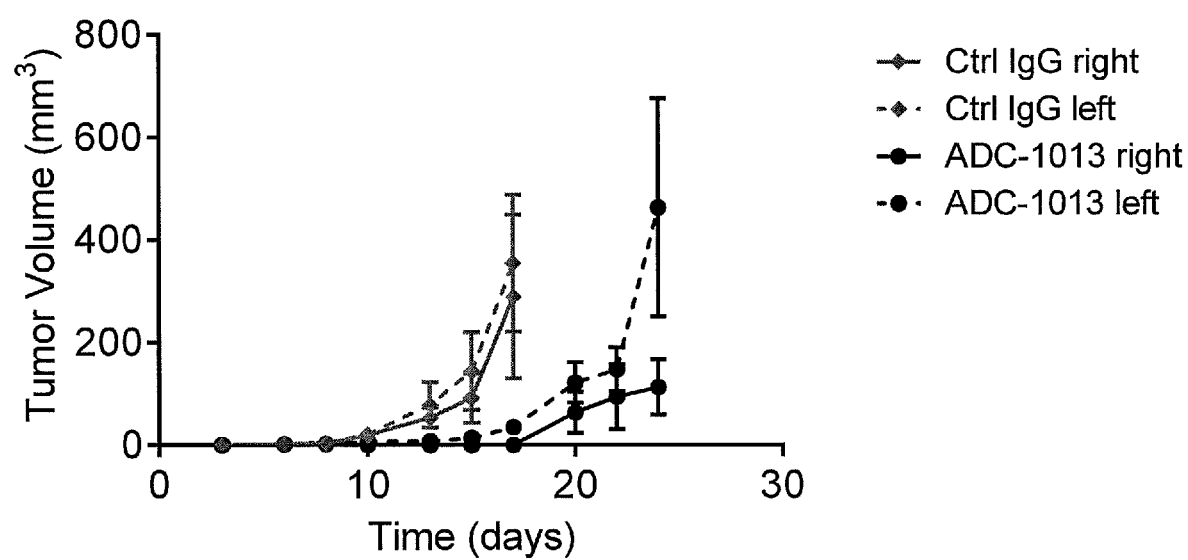
FIG. 11. Anti-tumor effect in B16.F10 melanoma cancer metastasis model. hCD40tg mice with one tumor on each flank received 100 µg ADC-1013 peritumorally in the tumor on the right flank, at day 3, 6 and 9 post tumor inoculation. Tumor volume over time for both the injected (right tumor) and non-injected (left) tumor is displayed in the figure.

The B16.F10 tumor cell line, growing in log phase, was injected subcutaneously at day 0 (D0) into the right flank and the left flank of hCD40 transgenic mouse (hCD40Tg) in a volume of 100 μL. The number of inoculated cells was $0.1 \times 10^6$ per mouse. The tumor growth was measured with a digital calliper in width, length and height of which the tumor volume was calculated (w/2×l/2×h/2×pi×(4/3)). The treatments were administered at days 3, 6 and 9. ADC-1013, and controls was administered intratumorally (100 μg per dose) into the tumor in the right flank. The tumor volume of both the injected and the non-injected tumor was followed over time as shown in FIG. 11.

Results and Conclusions

The local, intratumoral treatment also generated anti-tumor effects in the distal, non-injected tumor. The levels of free ADC-1013 following treatment of doses of 100 μg is well below the EC50 for ADC-1013 in in vitro assays, suggesting that the anti-tumor effect on the non-injected tumor in part is dependent migration of immune cells that are activated in the injected tumor area, to the non-injected tumor.

This suggests that ADC-1013 injected into one tumor can have significant anti-tumor effects on other, non-injected, tumors (e.g. metastases).

Example 11

Effect of Systemic (iv) Administration of ADC-1013

Material and Methods

The B16.F10(hCD40+) tumor cell line, growing in log phase, was injected subcutaneously at day 0 (D0) into the right flank of hCD40 transgenic mouse (hCD40Tg) in a volume of 100 μL. The number of inoculated cells was $0.1 \times 10^6$ per mouse. The tumor growth was measured with a digital calliper in width, length and height of which the tumor volume was calculated (w/2×l/2×h/2×pi×(4/3)). The treatments were administered at days 3, 6 and 9. ADC-1013 was administered intravenously (100 μg per dose).

Results and Conclusions

Figure 12:
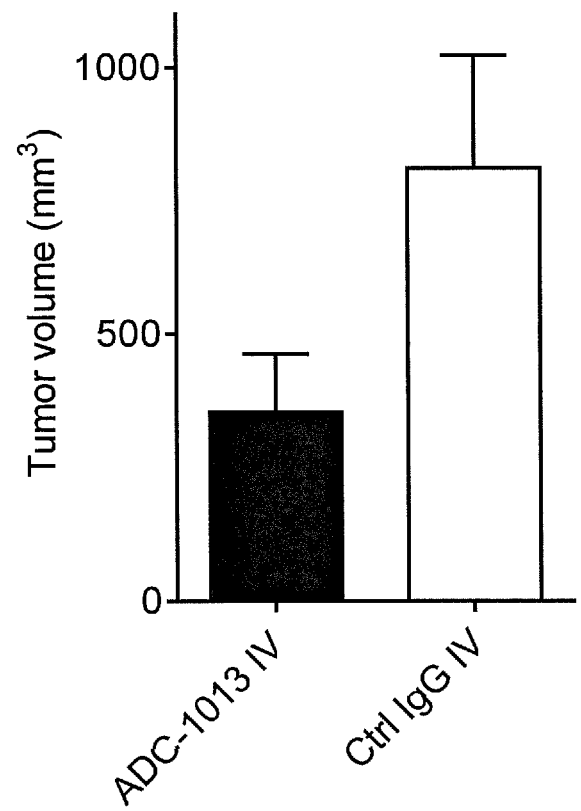
FIG. 12. Tumor volume at day 16. ADC-1013 was administered intravenously at day 3, 6 and 9 in hCD40tg mice with established melanoma tumors (B16.F10.hCD40+) 100 ug (n=12).

Systemic, intravenous administration of ADC-1013 resulted in a pronounced inhibitory effect on tumor growth (FIG. 12).

Example 12

In Vivo Effect of Combination Therapy III

Material and Methods

Female BalbC mice were inoculated subcutaneously with $5 \times 10^6$ A20 lymphoma cells. The mice were treated with 9D9 (anti-CTLA-4 antibody, BioXcel) peritumorally on day 5 and 8 and with the TLR agonist CpG (1668) intratumorally on day 5, 8 and 11. Survival was followed over time.

Results and Conclusions

Figure 13:
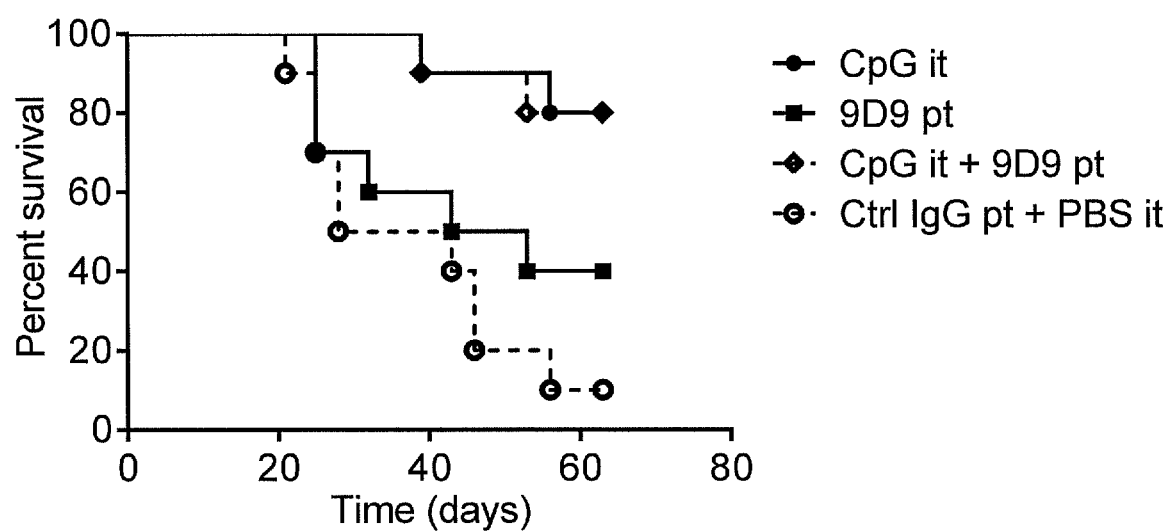
FIG. 13 shows an anti-tumour effect (measured by survival over time) in subcutanous A20 lymphoma tumours in BalbC mice. The mice were treated with 9D9 (anti-CTLA-4 antibody, BioXcel) peritumorally on day 5 and 8 and with the TLR agonist CpG (1668) intratumorally on day 5, 8 and 11.

The 9D9 antibody targets the checkpoint receptor CTLA-4 and CpG binds to Toll like receptor 9. TLRs are transmembrane proteins, expressed on antigen presenting cells, such as dendritic cells. Ligation of TLR9 with CpG induce activation of dendritic cells. Results are shown in FIG. 13.

The anti-tumour effect of the combination of treatments targeting TLR9 and CTLA4 does not results in an increased anti-tumor effect compared to treatment with CpG alone. The data thus show that a combination of a treatment that activates dendritic cells in combination with a checkpoint inhibitor does not always result in increased anti-tumour effects.

Accordingly, the efficacy of the combination therapies of the present invention could not have been predicted or reasonably expected.

The invention claimed is:

1. A method of treating a solid tumour in a subject comprising administering to the subject a therapeutically effective amount of a combination therapy comprising
   (a) an antibody, or antigen-binding portion thereof, that specifically binds to CD40, and
   (b) a further immunotherapeutic agent with efficacy in the treatment of cancer,
   wherein the antibody or antigen-binding portion thereof that specifically binds to CD40 comprises light chain CDR sequences of SEQ ID NOs: 1, 2 and 3 and heavy chain CDR sequences of SEQ ID NOs: 4, 5 and 6,
   wherein the further immunotherapeutic agent is an anti-PD-1 antibody which blocks the interaction between PD1 and PD-L1, and
   wherein the antibody or antigen-binding portion thereof that specifically binds to CD40 comprises the light chain constant region of SEQ ID NO: 11 and/or the heavy chain constant region of SEQ ID NO: 12.

2. The method according to claim 1 wherein the combination therapy provides a synergistic benefit in the treatment of a solid tumour in a subject.

3. The method according to claim 1 wherein the solid tumour is selected from the groups consisting of an adenoma, a blastoma, a carcinoma, a desmoid tumour, a desmopolastic small round cell tumour, an endocrine tumour, a germ cell tumour, a lymphoma, a sarcoma, a Wilms tumour, a lung tumour, a colon tumour, a lymph tumour, a breast tumour and a melanoma.

4. The method according to claim 3, wherein the solid tumour is a melanoma.

5. The method according to claim 1, wherein the antibody that specifically binds to CD40 comprises an intact antibody.

6. The method according to claim 1, wherein the antibody or antigen-binding portion thereof that specifically binds to CD40 comprises an antigen-binding fragment selected from the group consisting of: an Fv fragment and a Fab-like fragment.

7. The method according to claim 1, wherein the antibody or antigen-binding portion thereof is human or humanised.

8. A method of treating a solid tumour in a subject comprising administering to the subject a therapeutically effective amount of a combination therapy comprising
   (a) an antibody, or antigen-binding portion thereof, that specifically binds to CD40, and
   (b) a further immunotherapeutic agent with efficacy in the treatment of cancer,
   wherein the antibody or antigen-binding portion thereof that specifically binds to CD40 comprises light chain CDR sequences of SEQ ID NOs: 1, 2 and 3 and heavy chain CDR sequences of SEQ ID NOs: 4, 5 and 6,
   wherein the further immunotherapeutic agent is an anti-PD-1 antibody which blocks the interaction between PD1 and PD-L1, and
   wherein the antibody or antigen-binding portion thereof that specifically binds to CD40 comprises the light chain of SEQ ID NO: 7 plus SEQ ID NO: 11, and/or the heavy chain of SEQ ID NO: 8 plus SEQ ID NO: 12.

9. The method according to claim 1, wherein the anti-PD-1 antibody is selected from the group consisting of Nivolumab, Pembrolizumab, Lambrolizumab, and Pidilizumab.

10. The method according to claim 1, wherein components (a) and (b) are administered simultaneously or wherein component (b) is carried out between 24 hours and two weeks after component (a), between 24 hours and one week after component (a), between 24 and 72 hours after component (a), or between 24 and 48 hours after component (a).

11. The method according to claim 1, wherein component (a) is locally administered to the tumour site.

12. The method according to claim 1, wherein at least 30% of the amount of antibody is retained at the tumour site at four hours after administration.

13. The method according to claim 1, wherein component (b) is formulated as a composition suitable for systemic administration with at least one pharmaceutically acceptable diluent or carrier.

14. A method of treating a solid tumour in a subject comprising administering to the subject a therapeutically effective amount of a combination therapy comprising
   (a) an antibody, or antigen-binding portion thereof, that specifically binds to CD40, and
   (b) a further immunotherapeutic agent with efficacy in the treatment of cancer,
   wherein the antibody or antigen-binding portion thereof that specifically binds to CD40 comprises light chain CDR sequences of SEQ ID NOs: 1, 2 and 3 and heavy chain CDR sequences of SEQ ID NOs: 4, 5 and 6,
   wherein the further immunotherapeutic agent is an anti-PD-1 antibody which blocks the interaction between PD1 and PD-L1, and
   wherein component (a) is administered on multiple separate occasions and component (b) is administered such that exposure of the subject to the additional therapeutic agent is continuous for the duration of the method.

15. The method according to claim 1, wherein the subject is a human.

16. The method according to claim 8, wherein the combination therapy provides a synergistic benefit in the treatment of a solid tumour in a subject.

\* \* \* \* \*